(12) United States Patent
Schenker et al.

(10) Patent No.: US 11,524,118 B2
(45) Date of Patent: *Dec. 13, 2022

(54) DOSING MECHANISM FOR AN INJECTION DEVICE FOR ADMINISTERING A PRODUCT

(71) Applicant: Ypsomed AG, Burgdorf (CH)

(72) Inventors: Susanne Schenker, Langenthal (CH); Ursina Streit, Schönbühl (CH); Patrick Hostettler, Hasle (CH)

(73) Assignee: Ypsomed AG, Burgdorf (CH)

( * ) Notice: Subject to any disclaimer, the term of this patent is extended or adjusted under 35 U.S.C. 154(b) by 325 days.

This patent is subject to a terminal disclaimer.

(21) Appl. No.: 16/735,113

(22) Filed: Jan. 6, 2020

(65) Prior Publication Data
US 2020/0139052 A1    May 7, 2020

Related U.S. Application Data

(63) Continuation of application No. 15/262,824, filed on Sep. 12, 2016, now Pat. No. 10,537,685, which is a
(Continued)

(30) Foreign Application Priority Data

Mar. 13, 2014    (EP) .................................... 14159635

(51) Int. Cl.
    A61M 5/315    (2006.01)
    A61M 5/20    (2006.01)

(52) U.S. Cl.
    CPC ............ *A61M 5/3155* (2013.01); *A61M 5/20* (2013.01); *A61M 5/31541* (2013.01);
    (Continued)

(58) Field of Classification Search
    CPC ............ A61M 5/3155; A61M 5/31583; A61M 5/31553; A61M 5/20; A61M 5/31541;
    (Continued)

(56) References Cited

U.S. PATENT DOCUMENTS

| 5,104,380 A | 4/1992 | Holman et al. |
| 5,114,406 A | 5/1992 | Gabriel et al. |

(Continued)

FOREIGN PATENT DOCUMENTS

| EP | 0554995 A1 | 8/1993 |
| EP | 0554996 A1 | 8/1993 |

(Continued)

OTHER PUBLICATIONS

"International Preliminary Report on Patentability", Application No. PCT/CH2015/000026, dated Feb. 23, 2015, 9 pages.
(Continued)

*Primary Examiner* — Lauren P Farrar
(74) *Attorney, Agent, or Firm* — Dorsey & Whitney LLP

(57) ABSTRACT

A dosing mechanism for an injection device includes a dose-setting element with a first element coupled thereto, which, during dose setting, is rotatable relative to a second element about a main rotation axis in a first direction and, during dose discharge, is fixed in rotation relative to the second element. The first and the second elements are coupled via a sleeve-shaped stop element, which forms a stop abutment. The dosing mechanism includes a stop, and the stop abutment, during the rotation of the first element in the first direction, executes a movement to a stop position where the stop abutment strikes the stop and prevents rotation of the first element relative to the second element in the first direction of rotation. The sleeve-shaped stop element is rotatable about a secondary rotation axis, which is offset parallel to or offset at an angle to the main rotation axis.

21 Claims, 21 Drawing Sheets

Related U.S. Application Data continuation of application No. PCT/CH2015/000026, filed on Feb. 23, 2015.

(52) U.S. Cl.
CPC .... *A61M 5/31553* (2013.01); *A61M 5/31583* (2013.01); *A61M 5/31535* (2013.01); *A61M 5/31543* (2013.01); *A61M 5/31563* (2013.01)

(58) Field of Classification Search
CPC .......... A61M 5/31543; A61M 5/31535; A61M 5/31563
See application file for complete search history.

(56) References Cited

U.S. PATENT DOCUMENTS

| | | | |
|---|---|---|---|
| 6,582,404 B1* | 6/2003 | Klitgaard | A61M 5/31511 604/207 |
| 2016/0151580 A1* | 6/2016 | Oakley | A61M 5/24 604/207 |

FOREIGN PATENT DOCUMENTS

| | | |
|---|---|---|
| EP | 2918298 A1 | 9/2015 |
| EP | 2950853 B1 | 3/2017 |
| WO | 2002053214 | 7/2002 |
| WO | 2004078226 A2 | 9/2004 |
| WO | 2006076921 | 7/2006 |
| WO | 2006086983 A1 | 8/2006 |
| WO | 2009105910 | 9/2009 |
| WO | 2010149209 A1 | 12/2010 |
| WO | 2013170392 A1 | 11/2013 |
| WO | 2014117944 A1 | 8/2014 |
| WO | 2015135083 A1 | 9/2015 |

OTHER PUBLICATIONS

"International Search Report", Application No. PCT/CH2015/000026, dated Feb. 23, 2015, 5 pages.

* cited by examiner

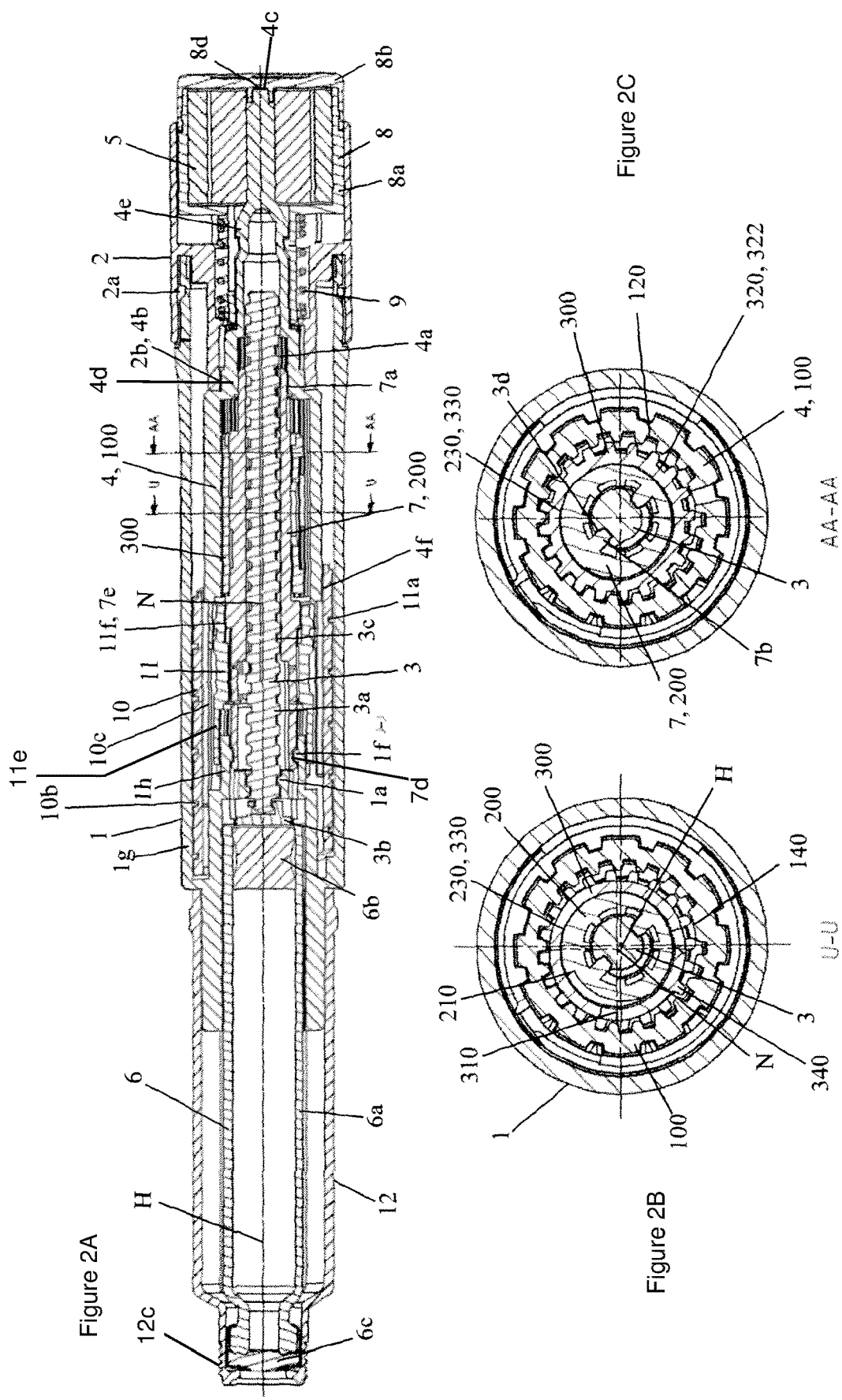

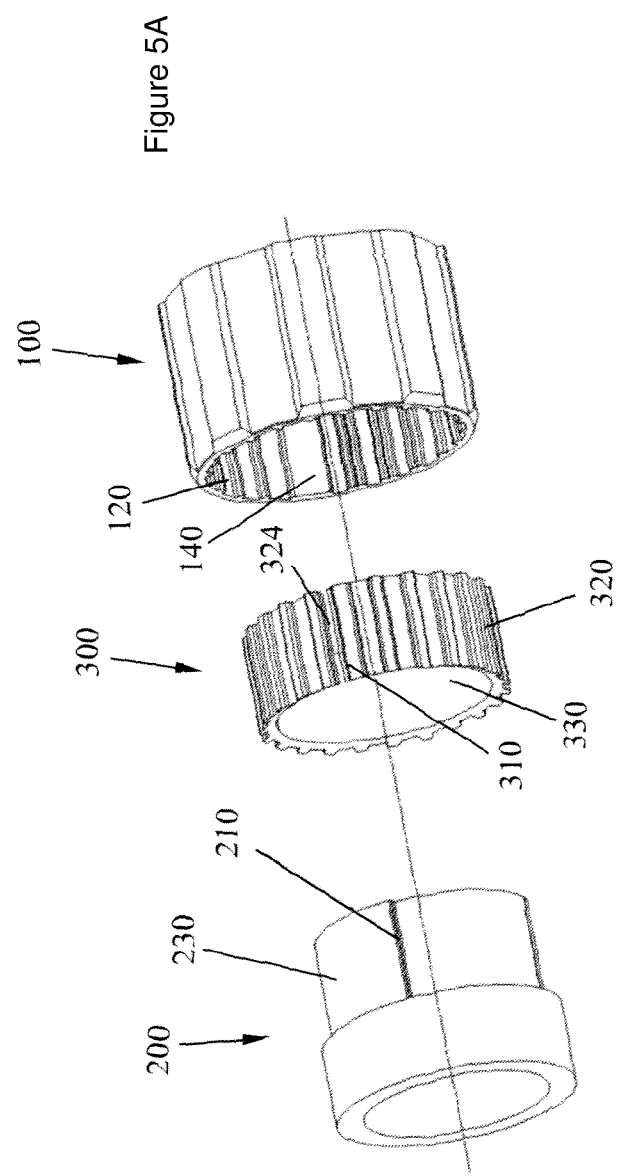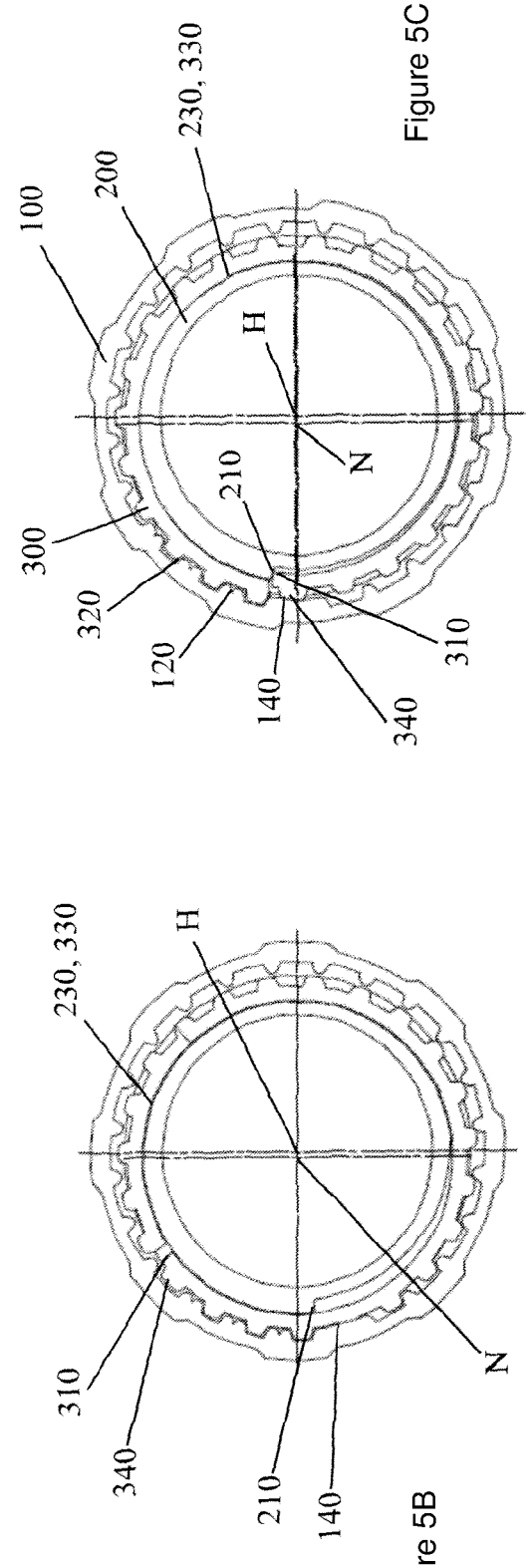

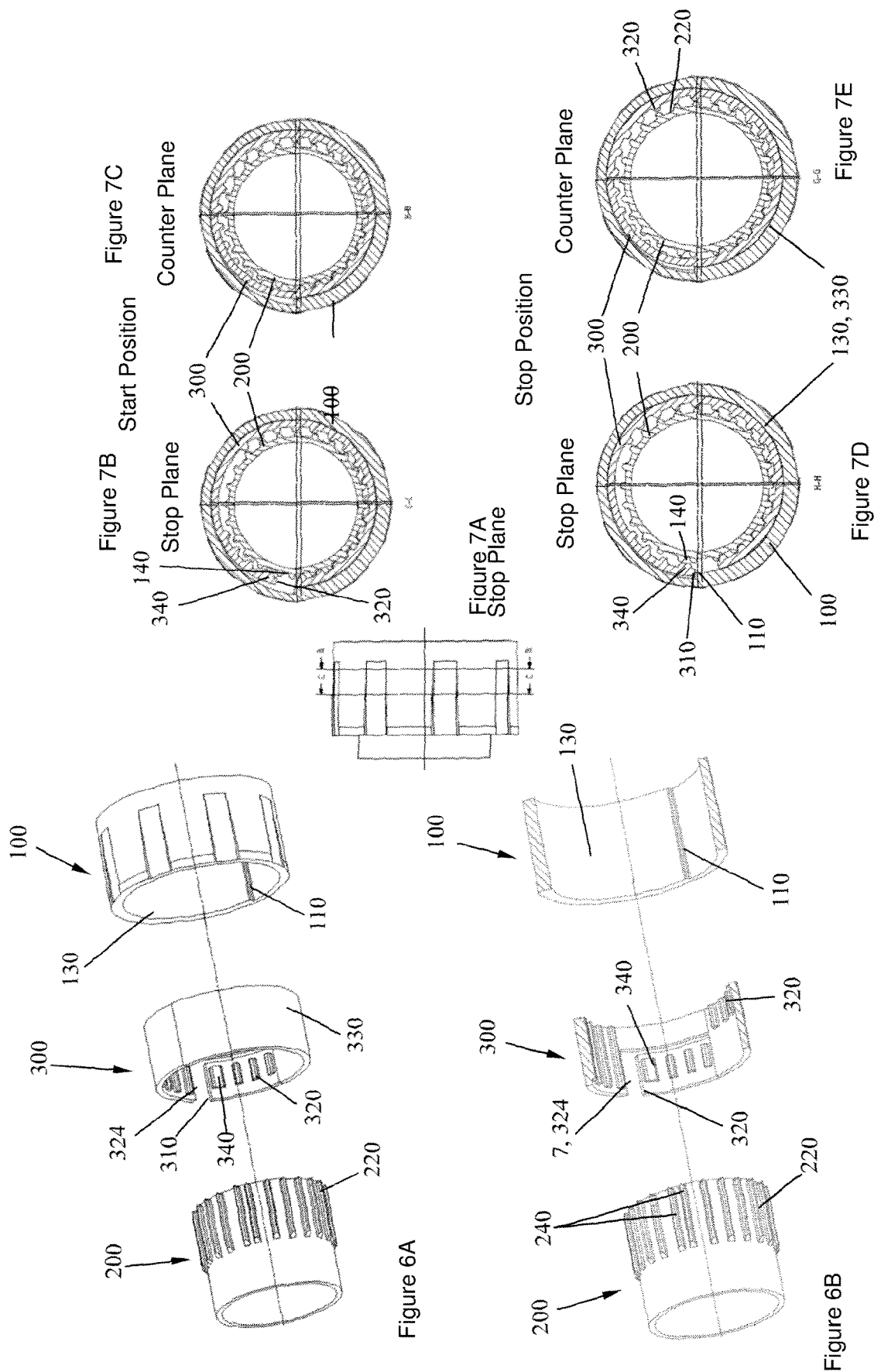

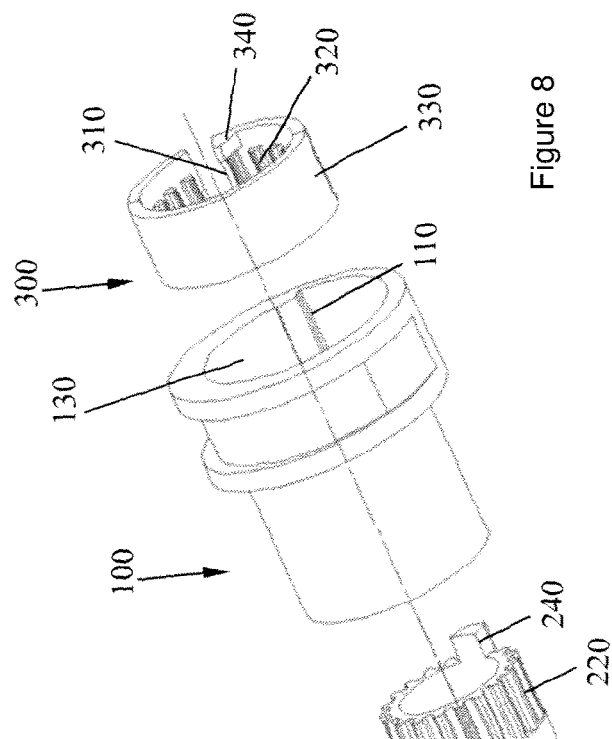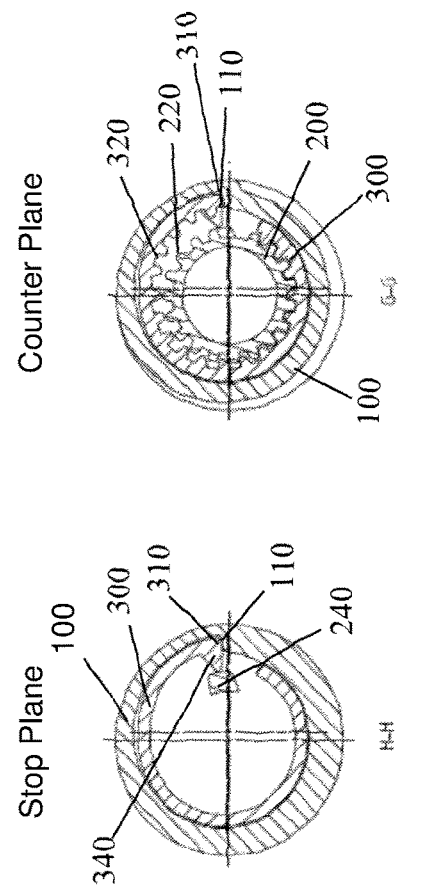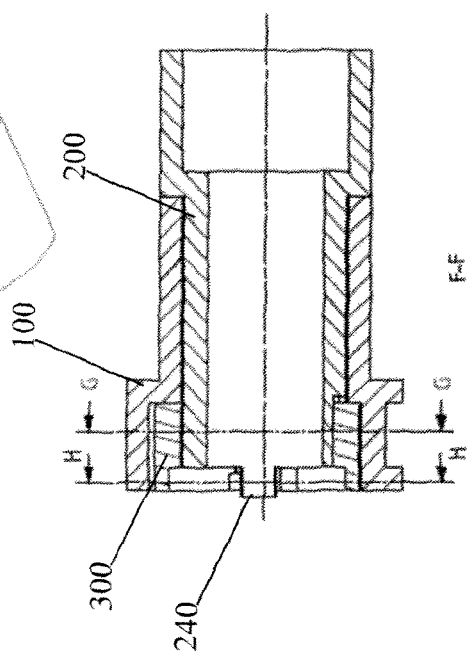

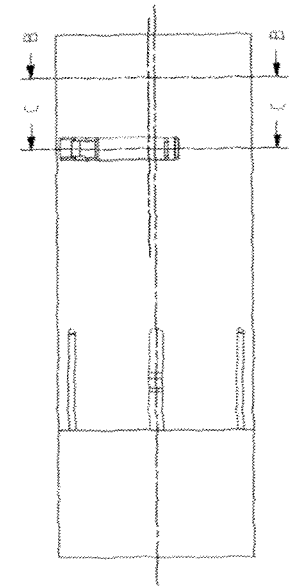
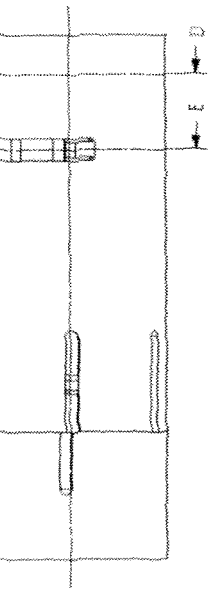
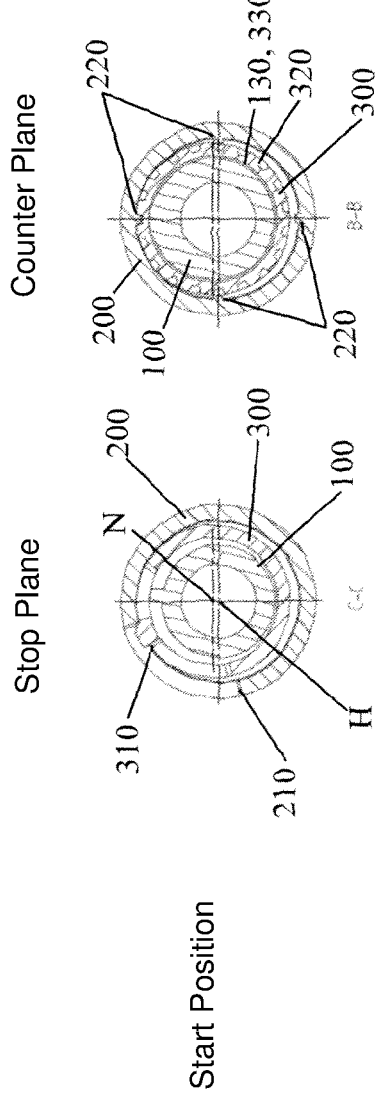
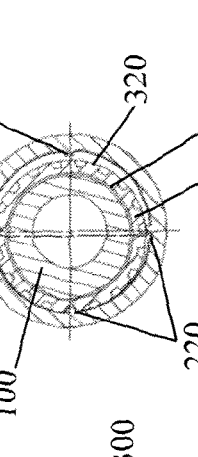
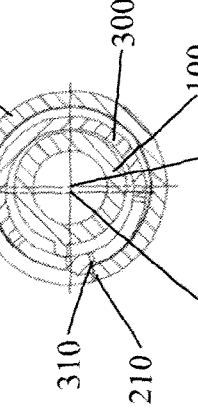

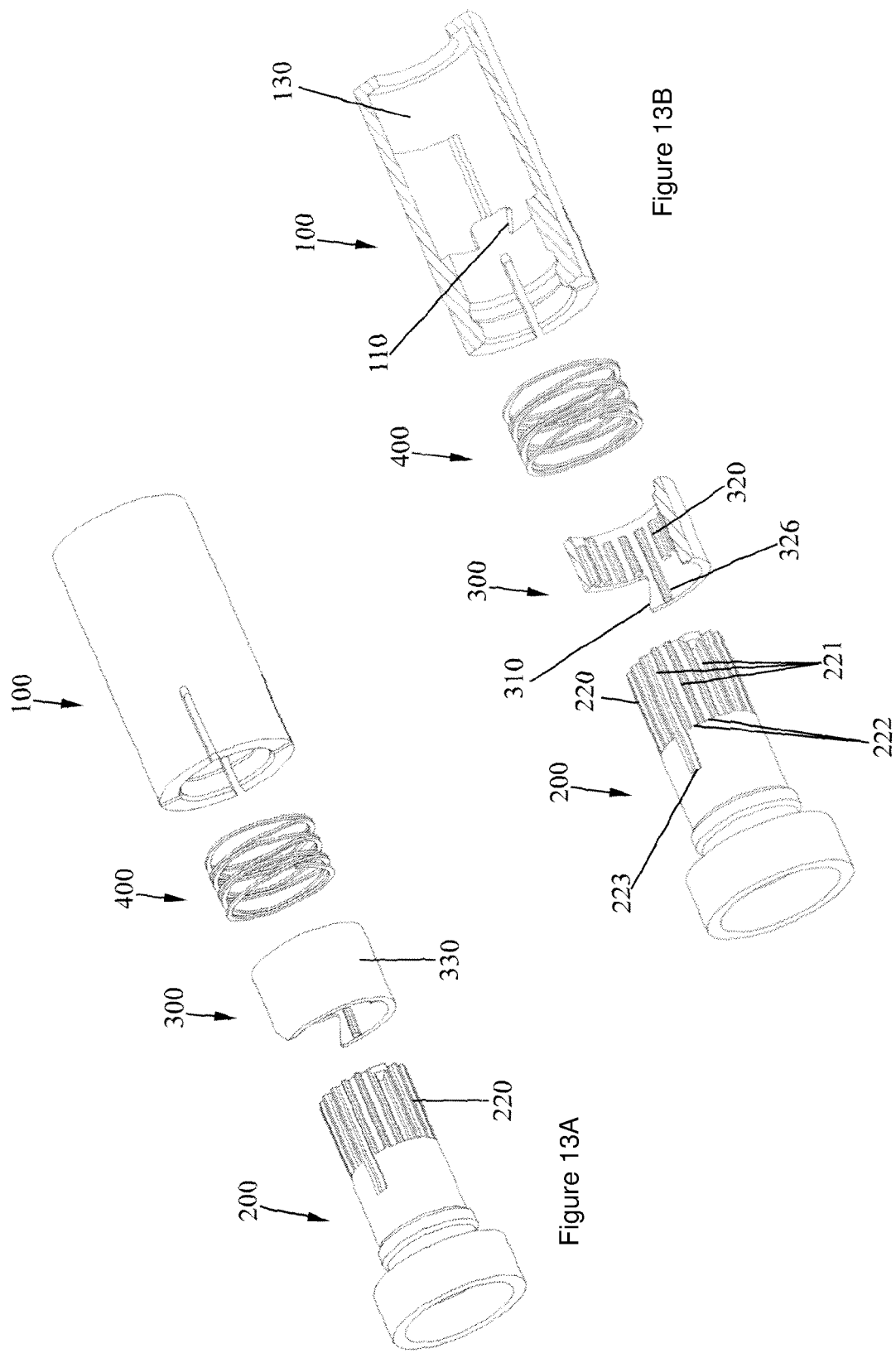

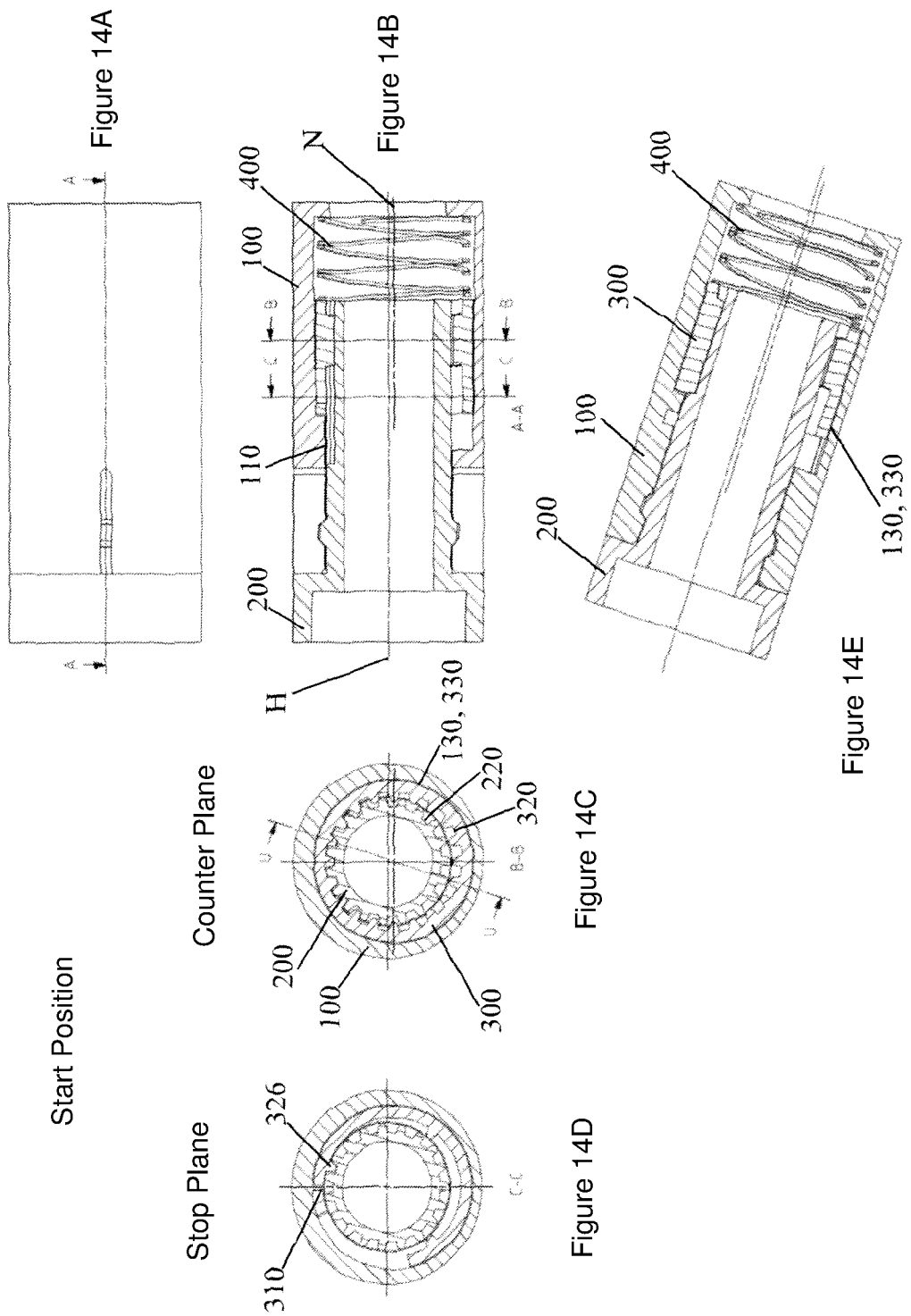

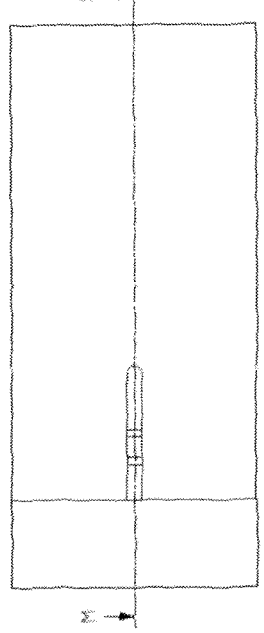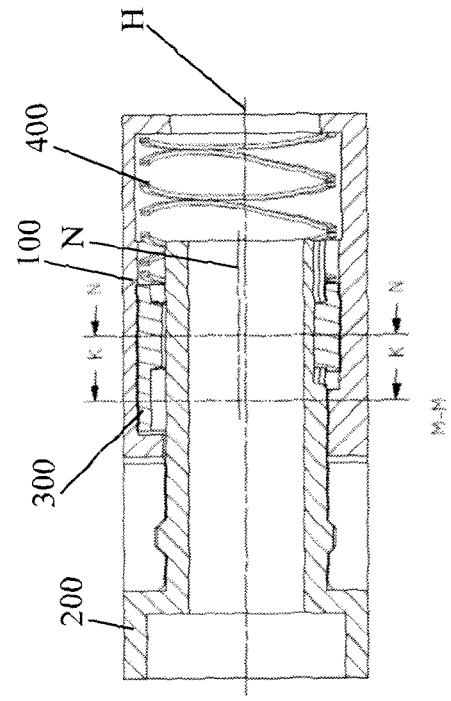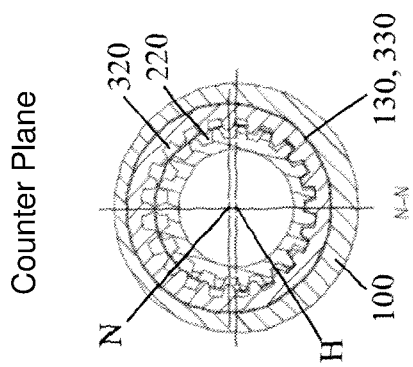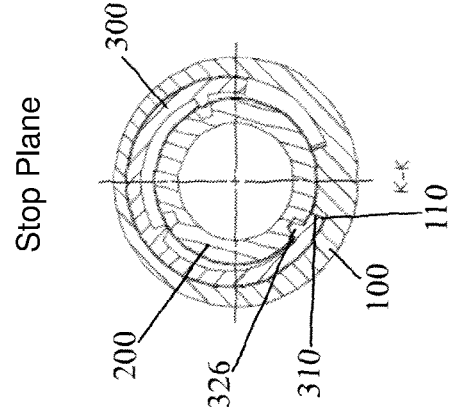

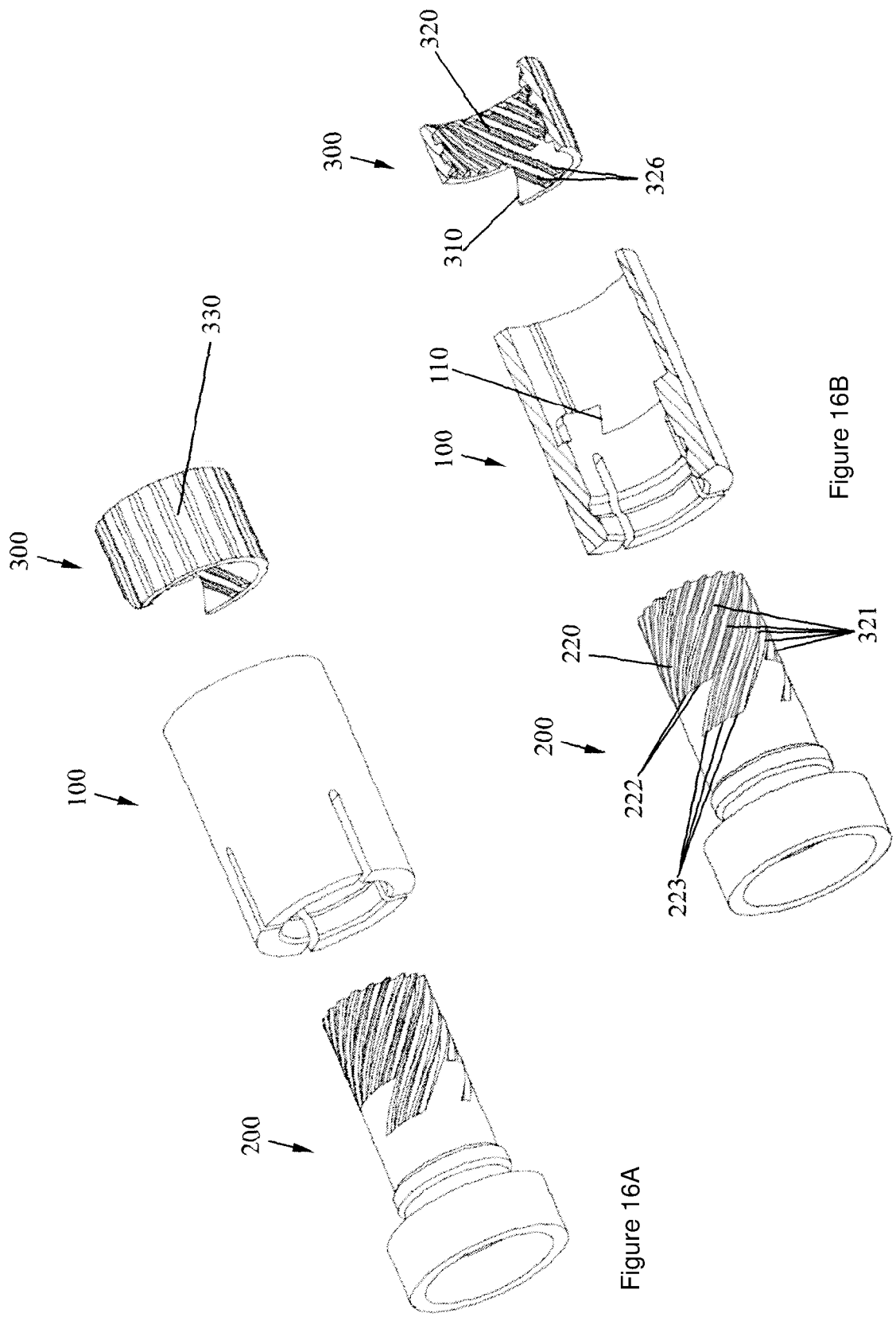

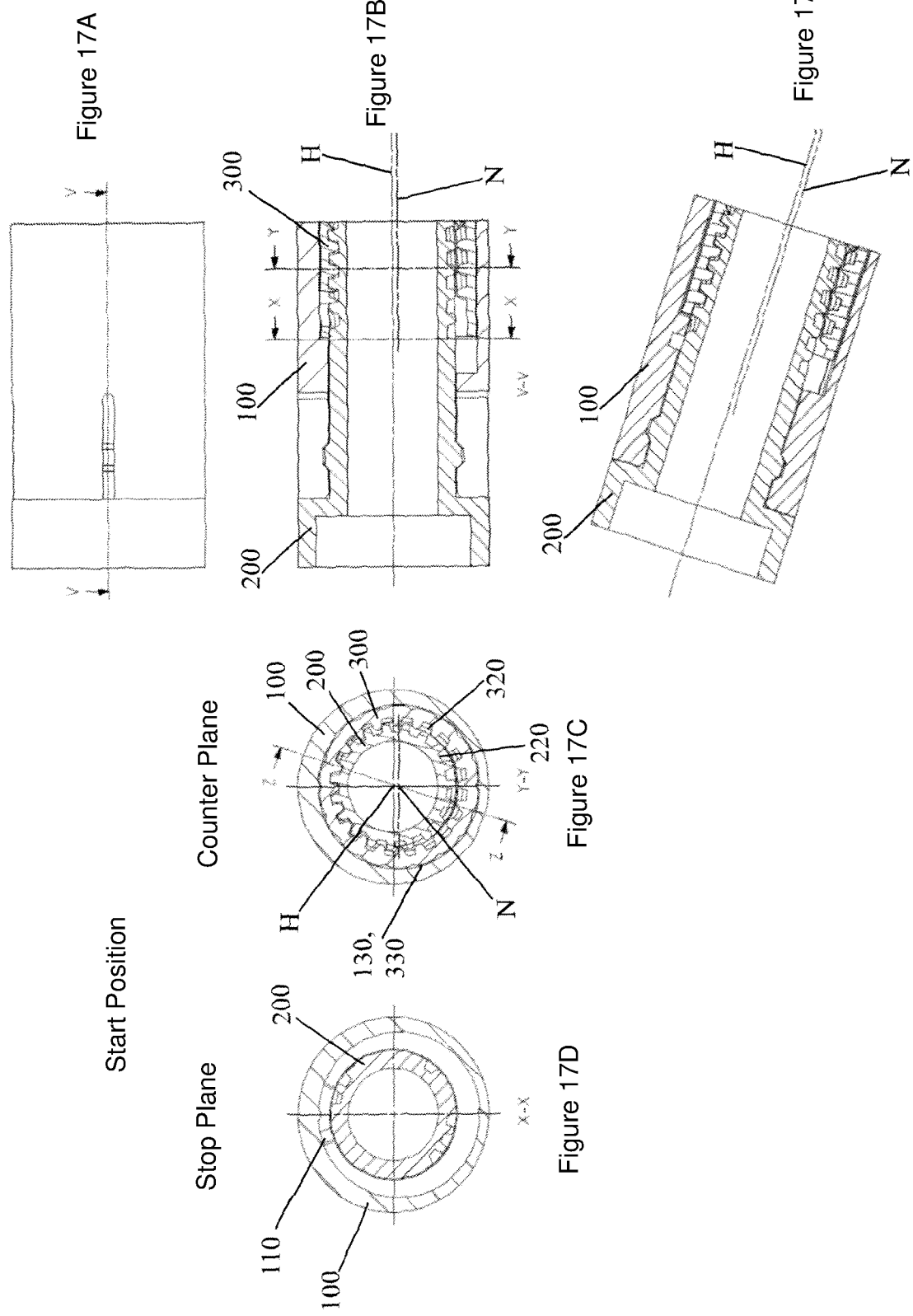

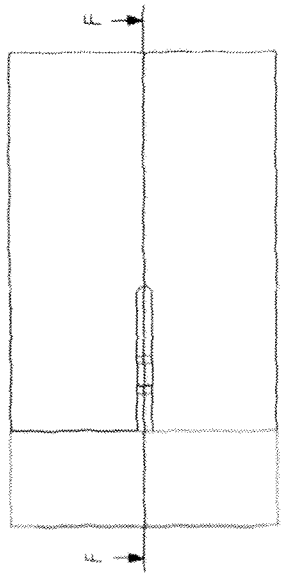
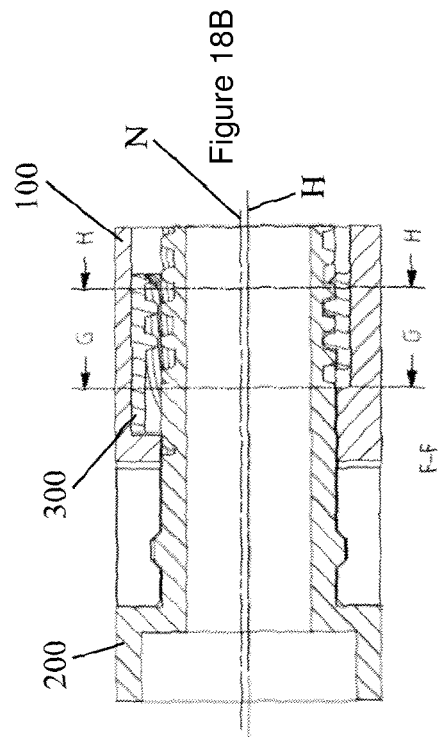
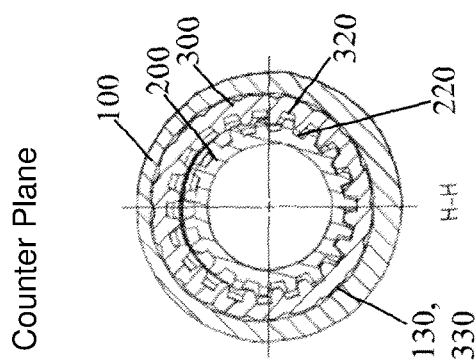
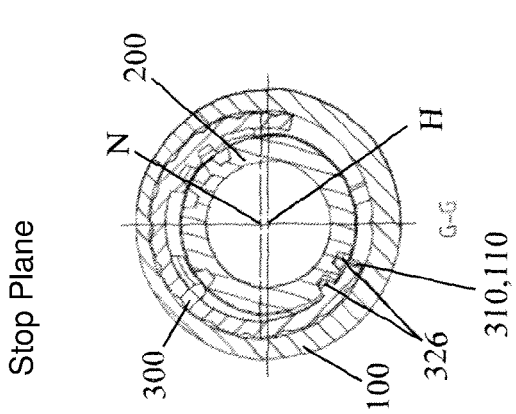

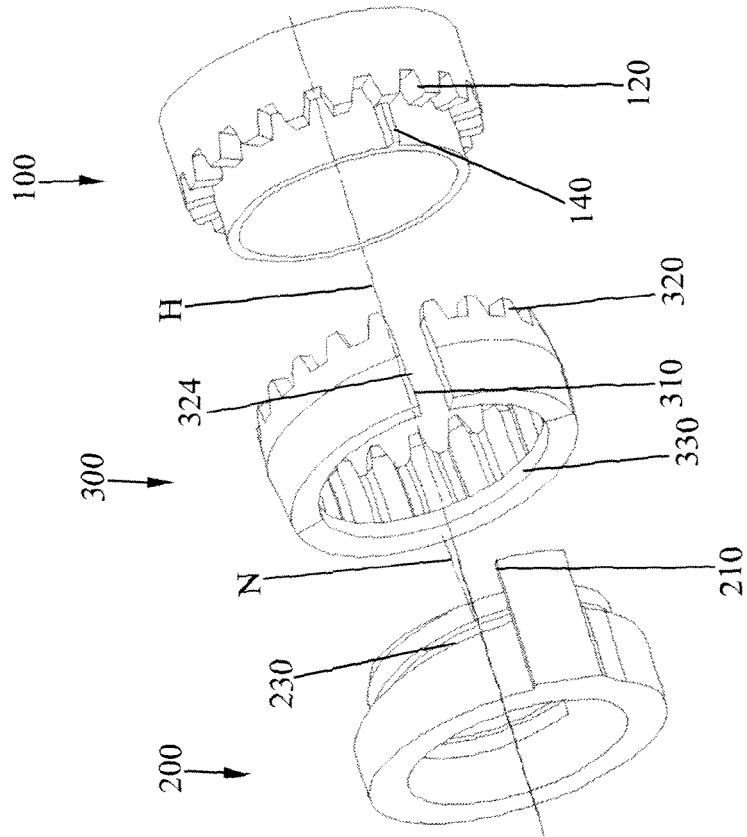

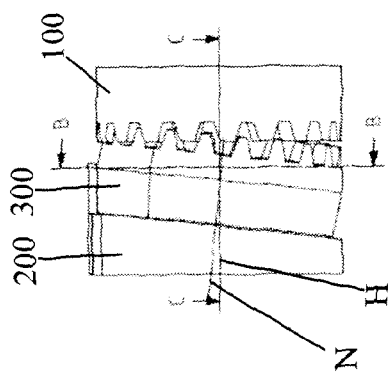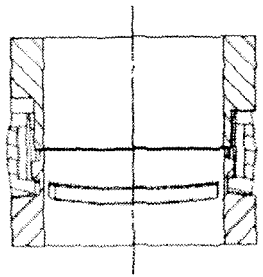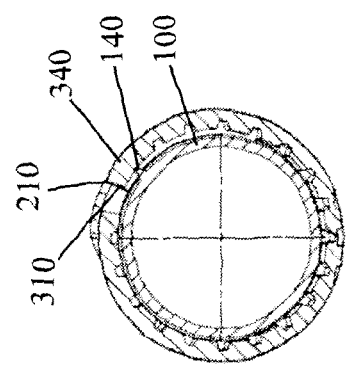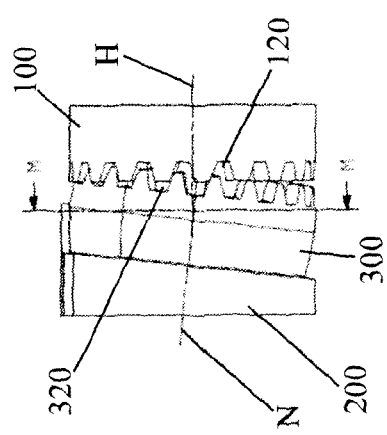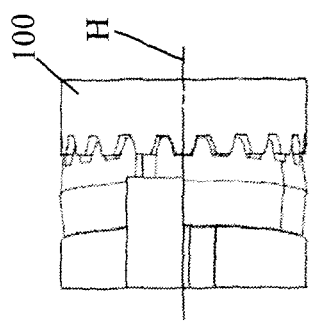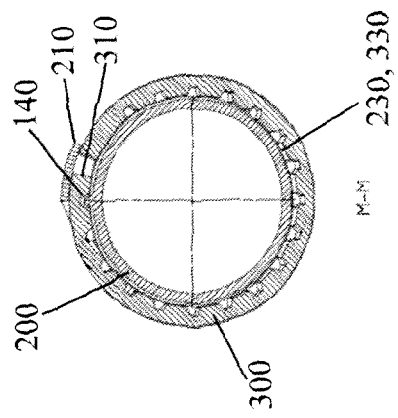

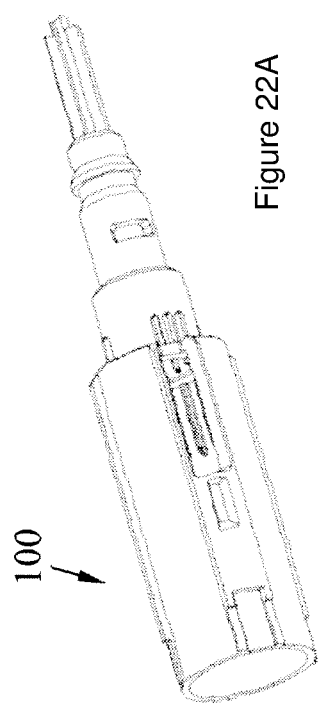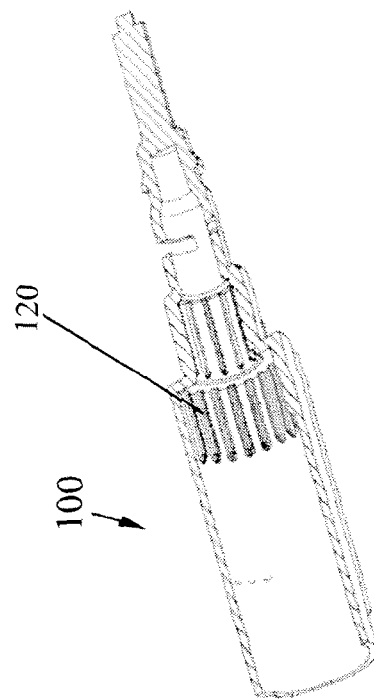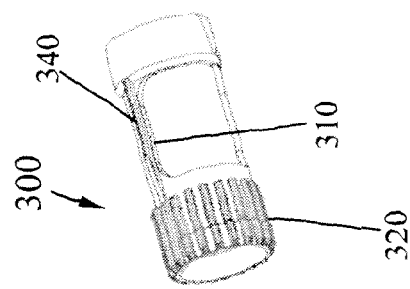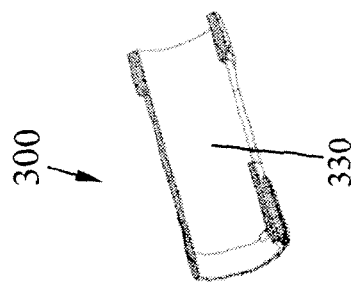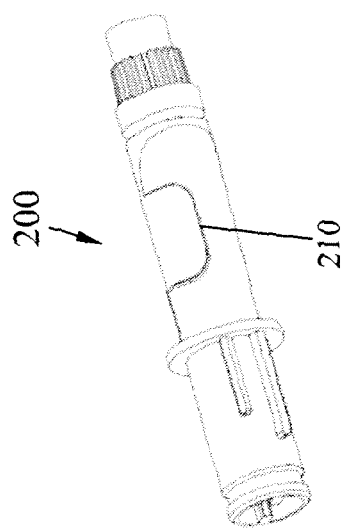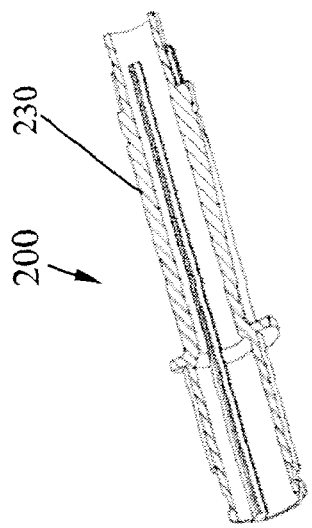

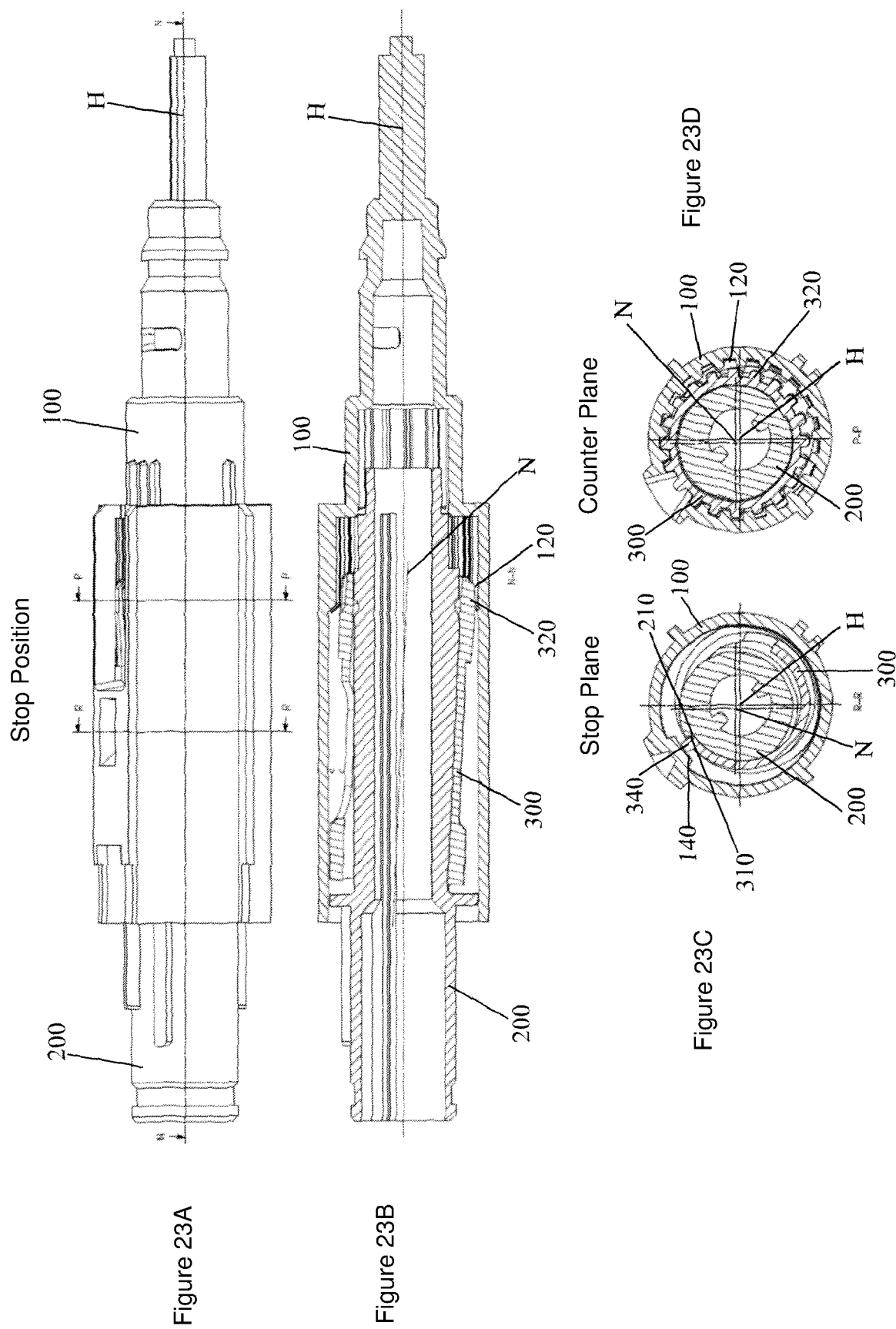

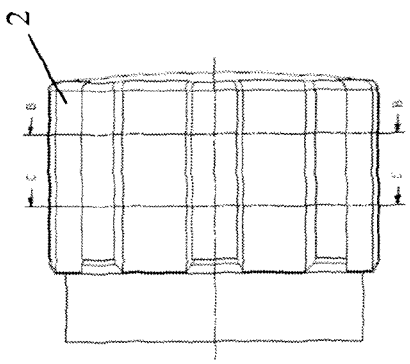
Figure 25A
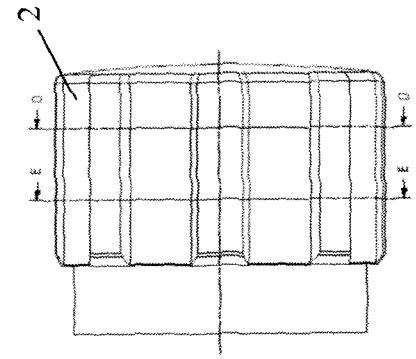
Figure 25D
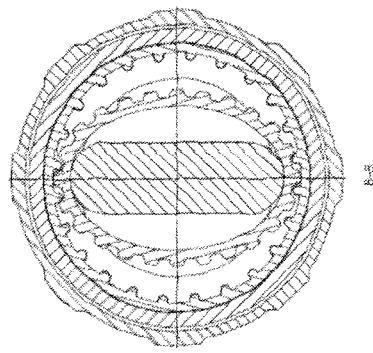
Figure 25B
Start Position
Figure 25E
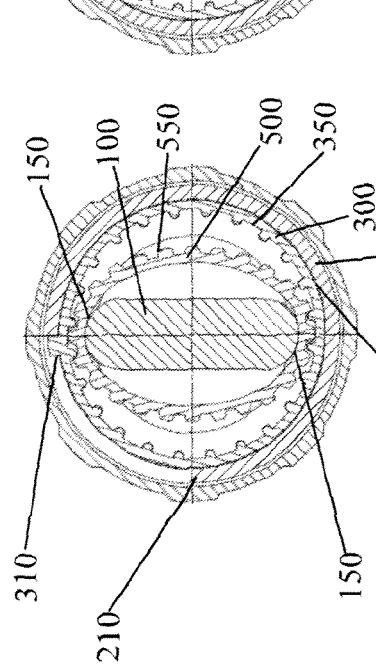
Figure 25C
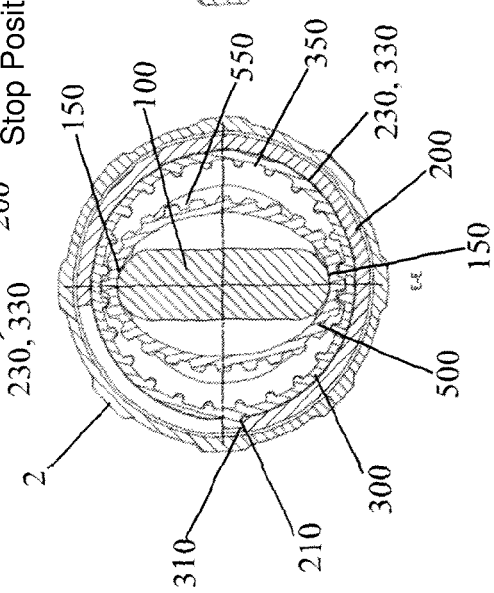
Stop Position
Figure 25F

DOSING MECHANISM FOR AN INJECTION DEVICE FOR ADMINISTERING A PRODUCT

CROSS-REFERENCE TO RELATED APPLICATIONS

This application is a Continuation of U.S. patent application Ser. No. 15/262,824 filed Sep. 12, 2016, issued as U.S. Pat. No. 10,537,685 on Jan. 21, 2020, which in turn is a continuation of International Patent Application No. PCT/CH2015/000026 filed Feb. 23, 2015, which claims priority to European Patent Application No. 14 159 635.3 filed Mar. 13, 2014. The entire contents of each are incorporated herein by reference for any and all purposes.

BACKGROUND

The invention relates to a dosing mechanism for an injection device, by means of which a preferably liquid product, in particular a medicament, can be administered or discharged. In particular, the invention also relates to an injection device comprising such a dosing mechanism. By means of the dosing mechanism, a dose to be administered can be set. The dosing mechanism can be part of a drive mechanism, so that it can preferably also be a dosing and drive mechanism. The mechanism can prevent the setting of a dose, which, for example, exceeds the quantity of a product to be administered in a product container of the injection device.

The term "medicament" here covers any free-flowing medicinal formulation that is suitable for controlled administration through a means such as, for example, a cannula or a hollow needle, comprising, for example, a liquid, a solution, a gel or a fine suspension containing one or more medicinal active substances. A medicament can be a composition with a single active ingredient or a premixed or co-formulated composition with several active ingredients from a single container. Medicaments include drugs such as peptides (for example, insulin, insulin-containing medicaments, GLP-1-containing as well as derived or analogous preparations), proteins and hormones, biologically obtained or biologically active ingredients, active ingredients based on hormones or genes, nutrient formulations, enzymes, and other substances both in solid (suspended) or liquid form, but also polysaccharides, vaccines, DNA or RNA or oligo-nucleotides, antibodies or parts of antibodies as well as suitable base, auxiliary and carrier substances.

In particular, the invention relates to a dosing mechanism that prevents the setting of a dose to be administered higher than a predetermined value. Thus, the setting of a dose can be prevented even when sufficient quantities for further injections are still present in the product container. As a result, it is advantageously possible to predetermine a desired dischargeable product quantity by means of the device and not by way of the total quantity contained in the product container.

From the prior art, numerous dosing mechanisms are known, which prevent the setting of a dose exceeding the medicament quantity in a reservoir of an injection device.

By means of injection devices known from the prior art, product doses can be set with a dosing mechanism and subsequently discharged from the product container. The case can occur in which a larger dose was set with a dose-setting element than can be discharged from the product container, since the product container contains a smaller product quantity than the dose that had been set. This can lead to the discharge of less product than had been set, which, depending on the discrepancy, can lead to varying degrees of problems for the patient.

For example, in the published, unexamined application WO 2004/078226 A2, a drive mechanism for drug administration apparatuses is described. This drive mechanism contains a housing, a dose-setting sleeve and a two-part piston rod. In an embodiment, a drive sleeve extends downward along an inner portion of the piston rod, when a dose is selected. The distance covered here corresponds to the discharge stroke of the piston needed for the dose. If a subsequent dose is selected, the drive sleeve continues to move along the piston rod. The position of the drive sleeve thus corresponds to the medicament quantity still contained in the cartridge. When the drive sleeve then reaches the end of a thread pitch on the inner portion of the piston rod and as a result cannot rotate further, this corresponds to an empty cartridge.

Another example is described in the published, unexamined application U.S. Pat. No. 6,582,404 B1, which shows a limitation mechanism for drug administration apparatuses, which prevents the setting of a dose that exceeds the residue remaining in the cartridge. The administration device has a dose-setting element, which, when a dose is set by turning relative to a driver, is moved away from a fixed abutment.

The dose-setting element is connected here to the driver in such a manner that it can be turned in a direction without also moving said driver. The dose is administered by turning the dose-setting element back, and the dose-setting element then also moves the driver. The turning driver causes a discharge movement of the piston rod. The driver is connected to a track whose length corresponds to the medicament quantity nominally contained in the cartridge. In this track, a track follower runs, which is connected to the dose-setting element. Each time a dose is selected, the track follower continues to move in the track. When the track follower has reached the end of the track, the dose-setting device cannot be turned further, and a dose-setting higher than the residue still remaining in the cartridge is prevented.

Another example of such an apparatus is described in EP 0 554 996 A1 and shows an injection device for administering liquid such as insulin into body tissues. This injection device contains a dose-setting mechanism, which has a units counter ring and a tens counter ring. A transmission member is provided in order to selectively couple the units counter ring to the tens counter ring, so that they turn together only in selected sections during the dose setting. The dose set is indicated by means of numbers on the rings. Furthermore, the injection device comprises a dose limiting mechanism, which limits the movement of a guide spindle for the provided piston movement in the cartridge, wherein protuberances in the plunger reach the end of grooves along the guide spindle and prevent further movement. The dose limiting mechanism is provided separately from the dose-setting mechanism.

Finally, WO 2006/086983 A1 shows an example of a dose-setting device for self-injection apparatuses with a dose limiting mechanism, which comprises two turning parts, wherein the first part turns continuously during the setting of a dose, and, after a certain rotation position has been reached, the second part in each case also turns in some sections via a selective coupling device. The result is that the second part turns discontinuously over a smaller angle than the first part. The turning of the second part is then limited by an abutment fixed to the housing, which prevents a dose-setting higher than the residue still remaining in the cartridge.

From WO 2010/149209 A1, an injection device is known, which comprises a dose-setting device and coupled to the latter an element, which, during a dose setting, can be rotated relative to another, second element and, which, during a dose discharge, is fixed in rotation relative to the second element. The first element and the second element are connected via a coupling member, which can be spherical, annular, nut-shaped or segment-shaped, for example. Furthermore, a stop abutment is provided, wherein, during a dose setting, the coupling member executes a movement to a stop position, wherein, in the stop position, the coupling element prevents the setting of a dose.

WO 2013/170392 A1 describes a dosing mechanism, which prevents the setting of a dose to be administered above a predetermined value in a reliable and space-saving manner. For this purpose, during the dose setting, a first and a second stop means can run in each case through a path. The paths described by the first and second stop means are self-enclosed and can be run through repeatedly by the first stop means and/or second stop means until, at the stop position, the stop means come in mutual abutment, as a result of which, during the dosing movement, a blocking of the movement of the limiting means relative to one another is achieved.

SUMMARY

The present invention is based on the problem of creating a dosing mechanism for setting a dose for an injection or infusion apparatus for administering a product, which prevents the setting of a dose to be administered higher than a predetermined value in a reliable, simple and even more space-saving manner, and which is constructed as stably as possible.

This problem is solved by the subject matter of the independent claims. Advantageous developments result from the dependent claims, the description and the figures.

The invention starts with a dosing mechanism for an injection device, wherein the central idea is that, during a dose setting, a first element coupled to a dose-setting element is rotatable relative to another, second element about a rotation axis in a first direction of rotation, and, during a dose discharge, it is fixed in rotation relative to the second element, wherein the first element and the second element are coupled via a stop element. For this purpose, a counter mechanism is formed, which acquires only the doses that are set during the dose setting. Since the first element and the second element are fixed in rotation relative to one another, when the set dose is discharged, the dose mechanism can remember the absolute value, i.e., the sum of all the set doses that have been discharged.

The dose-setting element can be coupled to or coupled directly to the first element. During the setting of the dose, the dose-setting element is preferably coupled to the first element in a rotationally fixed manner. In particular, the coupling can be released via a coupling, for example, when the set product dose is discharged. Alternatively, the dose-setting element can be coupled permanently in a rotationally fixed manner to the first element, in particular when the dose-setting element is or comprises a dose indicator sleeve or is at least connected to such a dose indicator sleeve.

For example, the function that the first element is rotatable relative to the second element during a dose setting and rotationally fixed during the dose discharge can be implemented by means of a coupling. This coupling can be disengaged or open during the dose setting, wherein it can be engaged or closed during the discharge. The coupling can comprise, for example, a first coupling structure, which is connected in a torque-proof manner to the first element, and, in particular, formed by the first element, and an additional, second coupling structure, which is engaged in a rotationally fixed manner in the second element, in particular, formed by the second element. The first coupling structure and the second coupling structure engage in a positive-locking manner with one another, when the coupling is engaged, so that the first coupling structure is arranged in a torque-proof manner relative to the second coupling structure. When the coupling is disengaged, the two coupling structures are rotatable relative to one another and preferably disengaged from the positive-locking connection. For example, an activation element, in particular an activation head, can be provided, which can be moved back and forth between a non-activated position and an activated position, for example, so that it is shiftable, wherein the activation element is connected to the coupling in such a manner that the coupling is disengaged in the non-activated position and engaged in the activated position. In particular, the disengaged coupling is engaged by the activation of the activation element, i.e., by moving or shifting the activation element from its non-activated position into the activated position. For example, the two coupling structures of the coupling can be shifted relative to one another, for example, along the rotation axis, when the activation element is activated or released. For example, a spring can be provided, which holds the coupling in its disengaged switching state and/or the activation element in its non-activated position. The spring can be tensioned by engaging the coupling. When the activation element is activated, the spring can be tensioned, wherein the tensioned spring of the activation element resets into a non-activated position and/or the coupling is disengaged, when the activation element is moved from the activated position into the non-activated position, in particular, released by the user of the dosing mechanism.

The activation element can be, for example, an activation button that is arranged at the proximal end of the device facing the distal end on which an injection needle can be arranged, or that forms the proximal end. The activation element can be pushed with a finger, in particular, the thumb of the hand of the user, which grips a housing of the dosing mechanism or of the injection device comprising the dosing mechanism, i.e., it can be activated or shifted from the non-activated position into the activated position. By releasing the activation element, the spring can reset the activation element back into the non-activated position.

The first, preferably sleeve-shaped element, and the second, preferably sleeve-shaped element are coupled via a stop element, which is, in particular, sleeve-shaped, and which forms a stop counter abutment. In particular, the first element and the second element each can be in contact with the sleeve-shaped stop element.

It is particularly preferable that the sleeve-shaped stop element can surround one of the first element and second element, wherein, for example, the other of the first and second element can surround the sleeve-shaped stop element. For example, between the first element and the second element, an annular slot can be formed, in which the sleeve-shaped stop element is arranged. Due to the fact that the sleeve-shaped stop element surrounds the first element or the second element, a particularly stable design is achieved. In particular, the sleeve-shaped stop element can surround a piston rod or form a passage for the piston rod. The piston rod is moved into a discharge position for discharging the product dose. As a result, a compact construction design can be achieved; in particular, the construction length of the dosing mechanism can be reduced or kept small.

The dosing mechanism has a stop abutment, wherein, during the turning of the first element in the first direction of rotation, the stop counter abutment executes a movement towards a stop position, wherein, in the stop position, the stop counter abutment strikes the stop abutment, and prevents the rotation of the first element relative to the second element in the first direction of rotation. As a result, the first element is prevented from moving further in the first direction of rotation, i.e., the direction of rotation that would result in an increase in the dose to be discharged. The stop counter abutment can comprise a stop counter abutment surface, and the stop abutment can comprise a stop abutment surface, wherein these surfaces are in contact when the stop counter abutment strikes the stop abutment.

For example, for dosing, i.e., for increasing the dose to be discharged, the dose-setting element can be turned in the first direction of rotation by the user of the device, and, for decreasing the dose, also referred to as dose correction, in a second direction of rotation opposite the first direction of rotation, in particular, with respect to the second element and/or a housing, in which the first element, the second element and the stop element can be arranged. The housing can be sleeve-shaped, for example, in particular, cylindrical, and it can surround or receive the first and second elements as well as the stop counter abutment.

For example, the dose-setting element can be turned relative to the housing in the first and/or second direction of rotation.

In a first aspect, the sleeve-shaped stop element can be rotatable about a secondary rotation axis that is parallel offset or angularly offset with respect to the main rotation axis about which the first element is rotatable relative to the second element. The secondary rotation axis is the rotation axis of the sleeve-shaped stop element. The main rotation axis is the rotation axis of the first element. In particular, the main rotation axis can correspond to the central axis of the housing, of the first element, of the second element, and optionally of the piston rod.

The fact that the secondary rotation axis is arranged parallel offset with respect to the main rotation axis means that the secondary rotation axis is arranged eccentrically with respect to the main rotation axis. The fact that the secondary rotation axis is arranged angularly offset with respect to the main rotation axis means that the secondary rotation axis is in a mutual arrangement at an angle greater than 0°, in particular at an acute angle, i.e., at an angle greater than 0° and less than 90°. The main rotation axis and the secondary rotation axis can intersect one another or be arranged at an inclination with respect to one another. For example, the secondary rotation axis can alternatively be arranged at a right angle with respect to the main rotation axis; in particular, it can intersect the main rotation axis or be arranged at an inclination with respect to the main rotation axis. At an inclination means that the main rotation axis and the secondary rotation axis do not intersect one another and are not arranged parallel to one another.

Since the secondary rotation axis is arranged parallel offset or angularly offset with respect to the main rotation axis, the stop element of one of the first element or second element can come in contact at only one site of its periphery, in particular in its engagement area. The remaining, in particular, the largest portion of the periphery of the stop element does not come in contact with the first or the second element. As a result of this arrangement, it is advantageously achieved that the periphery with which the stop element comes in contact at the one site is, in particular, greater than or smaller than the periphery of the stop element. As a result, it is achieved advantageously that the stop element and the first or second element, which comes in contact with the stop element at the one site, turn with the same peripheral speed but with different angular speeds. As a result, in a manner similar to the one described in WO 2013/170392 A1, it is achieved that, during the turning of the first element relative to the second element, a point, in particular a switch structure that is formed by the element, which comes in contact with the stop element at the one site, and a point, in particular a switch counter structure, which is formed by the stop element, in each case describe a path such that the two paths intersect in at least one site, or come so close that the points come sufficiently close to one another so as to be in mutual abutment. This abutment has the effect, for example, that a turning of the first element relative to the second element in the first direction is blocked, or that the stop counter abutment is deflected, in particular transversely, with respect to the peripheral direction.

The paths described by the first and second point can be self-enclosed, in particular circular, and they can be traversed, preferably repeatedly, by the first point, by the second point, or by the two points until the points come into mutual abutment.

For example, the stop element can comprise a first engagement structure, in particular a toothing (e.g., teeth), arranged over its periphery concentrically about the secondary rotation axis, and one of the first element and the second element can comprise a second engagement structure, in particular a second toothing, arranged over its periphery and concentrically about the main rotation axis wherein the first engagement structure and the second engagement structure engage into one another in a positive-fitting connection, in particular intermesh, at a site of the periphery, i.e., in the engagement area. Outside of the engagement area, i.e., over the larger area of the periphery of the stop element, the first engagement structure and the second engagement structure do not engage in one another.

To the extent that each of the first engagement structure and the second engagement structure is a toothing arranged over the periphery, the pitch circles of these toothings can preferably be of different size.

In particular, the stop element is mounted eccentrically with respect to the main rotation axis and/or concentrically about the secondary rotation axis, in particular mounted slidingly, on the element of the first element and the second element that is not in engagement with the stop element with the above-mentioned engagement structure.

For example, the stop element can have a first sliding surface, and the other element of the first element and the second element can have a second sliding surface, wherein at least one of the first sliding surface and the second sliding surface is, preferably the two sliding surfaces are, arranged concentric about the secondary rotation axis. During the turning of the first element, the first sliding surface and the second sliding surface can slide off one another rotatingly. The first sliding surface can extend at least partially, preferably at least over most of the periphery, or completely over the periphery of the stop element. The second sliding surface can extend at least partially, preferably at least over the most of the periphery, or completely over the periphery of the first or second element. The element with the second sliding surface can be sleeve-shaped, for example, wherein it can have at least one section extending concentrically about the main rotation axis, and a section, namely the sliding surface, extending concentrically about the secondary rotation axis.

The stop abutment can be formed from the first element or the second element. For example, the stop abutment can be formed by a step formed on the inner or outer periphery that forms the second sliding surface. Alternatively, the stop abutment can be formed by a protrusion, wherein, between the protrusion and the second sliding surface, a slot can be formed, in which, for example, the stop element or a portion of the stop element can be arranged.

In preferred embodiments, the stop counter abutment can be arranged in a manner so it can be deflected, in particular slid or preferably resiliently deflected, transversely with respect to the peripheral direction, in particular on the stop element. This means that the stop counter abutment can be deflected approximately radially outward or radially inward, i.e., away from the secondary rotation axis or towards the rotation axis.

In additional embodiments, the stop element, including a stop counter abutment formed, for example, rigidly thereon, and/or the secondary rotation axis can be tilted about a tilt axis, which is arranged transversely, for example, approximately perpendicularly, with respect to the main rotation axis and the secondary rotation axis, into a deflected position, in which the secondary rotation axis is arranged angularly offset with respect to the main rotation axis, as a result of which the stop counter abutment faces the stop abutment in peripheral direction. The tilting can be achieved in that the switch structure and the switch counter structure strike one another. In the undeflected position, from which the stop element is tilted, the secondary rotation axis can be offset, for example, parallel with respect to the main rotation axis or it can be tilted freely about the main rotation axis. When the switch structure and the switch counter structure strike one another, the tilting of the stop element and of the secondary rotation axis is forced. Preferably, the first engagement structure of the stop element, and the switch counter structure are apart from one another along the secondary rotation axis. The result of this is that a tilting moment is generated about the tilt axis, when the switch structure and the switch counter structure strike one another.

In general, one of the first element and the second element can have a switch structure, which, in particular, forms the point or is the point that can traverse the path, for example repeatedly. The switch structure can deflect the stop counter abutment, on which, in particular, a switch counter structure is formed, during the turning of the first element transversely with respect to the peripheral direction, i.e., for example, radially inward or outward, in particular deflect or tilt resiliently or slidably, so that the stop counter abutment faces the stop abutment. In other words, this means that, in a first undeflected position, the stop counter abutment is at another radial distance from the secondary rotation axis or main rotation axis from that of the stop abutment. In the second, deflected position of the stop counter abutment, the stop counter abutment and the stop abutment are at approximately the same distance from the secondary rotation axis, so that they face one another, which has the effect that the stop counter abutment strikes the stop abutment or is pushed against the stop abutment, when the first element is turned in the first direction of rotation. The advantage of a deflectable or tiltable stop counter abutment is that the stop counter abutment can be turned at least once or even repeatedly past the stop abutment and strike the stop abutment only when the switch structure comes in contact with the switch counter structure or, in general, the switch structure moves the stop counter abutment from the first undeflected position into the second deflected position.

For example, the stop counter abutment can be formed on the stop element on a resilient arm that extends, for example, in peripheral direction of the stop element.

For example, the first engagement structure can be formed on the outer periphery of the stop element, wherein the second engagement structure can be formed on the inner periphery of the first element or of the second element. When the second engagement structure is formed on the inner periphery of the first element, the first sliding surface can be formed on the inner periphery of the stop element and the second sliding surface can be formed on the outer periphery of the second element. When the second engagement structure is formed on the inner periphery of the second element, the first sliding surface can be formed on the inner periphery of the stop element and the second sliding surface can be formed on the outer periphery of the first element.

Alternatively, the first engagement structure can be arranged on the inner periphery of the stop element, wherein the second engagement structure can be formed on the outer periphery of the first element or of the second element. When the second engagement structure is formed on the outer periphery of the first element, the first sliding surface can be formed on the outer periphery of the stop element, and the second sliding surface can be formed on the inner periphery of the second element. When the second engagement structure is formed on the outer periphery of the second element, the first sliding surface can be formed on the outer periphery of the stop element, and the second sliding surface can be formed on the inner periphery of the first element.

In a preferred example, the second engagement structure can be arranged over the inner periphery of the first element, wherein the first engagement structure can be arranged over the outer periphery of the stop element. The first engagement structure can have a first section and a second section, which are offset with respect to one another along the secondary rotation axis and, for example, spaced apart. The stop counter abutment can be arranged between the first section and the second section, in particular on the arm such as, for example, on a resilient tongue. The second element can form, for example, the stop abutment and/or the stop abutment can surround the second element.

In an additional preferred example, the second engagement structure can be arranged over the inner periphery of the first element, wherein the first engagement structure can be arranged over the outer periphery of the stop element, wherein, along the secondary rotation axis, the sleeve-shaped stop element has a partial or preferably continuous slot, i.e., a slot that is continuous from the proximal end to the distal end of the sleeve-shaped stop element. One of the walls bordering the slot of the stop element, i.e., one of the slot walls, can form the stop counter abutment, in particular the stop counter abutment surface. It is preferable that the second element form the stop abutment and/or that the stop element surround the second element.

In an additional preferred example, the second engagement structure can be arranged over the outer periphery of the second element, wherein the first engagement element is arranged over the inner periphery of the stop element. In a manner similar to the preceding example, the sleeve-shaped stop element can have, along the secondary rotation axis, a partial or preferably continuous slot, wherein one of the walls of the stop element bordering the slot forms the stop counter abutment. Preferably, the first element forms the stop abutment or the stop element surrounds the second element.

In particular, the stop element can have a switch counter structure that is arranged on its inner periphery and offset from the first engagement structure, and that is preferably in the shape of a protuberance. The second element can have a switch structure that is offset from the second engagement structure and, in particular, in the shape of a second protuberance. During the turning of the first element, the switch structure, in particular the second protuberance, can resiliently deflect the switch counter structure, in particular the first protuberance, and the stop counter abutment transversely with respect to the peripheral direction, namely when the switch structure comes in contact with the switch counter structure, so that the stop counter abutment faces the stop abutment formed by the first element.

In an additional example, the second engagement structure can be arranged over the inner periphery of the second element, wherein the first engagement structure can be arranged over the outer periphery of the stop element. The stop counter abutment can be arranged along the secondary rotation axis offset with respect to the first engagement structure, in particular on the resilient arm, for example, on a resilient tongue. It is preferable that the second element form the stop abutment and/or that the stop element surround the first element.

In yet another example, the second engagement structure can be arranged over the outer periphery of the second element, wherein the first engagement structure can be arranged over the inner periphery of the stop element, wherein the second engagement structure has a plurality of guide tracks arranged over the periphery, each having a front-side end. The end of at least one of the guide tracks can be arranged along the main rotation axis or the secondary rotation axis offset with respect to the ends of the other guide tracks. The end of the at least one guide track can thus be arranged in different positions with respect to the ends of the other guide tracks relative to the main or secondary rotation axis. The guide tracks can extend parallel to or helically about the main or secondary rotation axis. The first engagement structure or the stop element can comprise an engagement element, wherein the stop element is movable along the main rotation axis or the secondary rotation axis relative to the second element, when the engagement element is arranged in the at least one guide track, whose end is offset with respect to the other or remaining ends of the other or remaining guide tracks. When the engagement element is in this at least one guide track, the stop element can be shifted along the secondary or main rotation axis, as a result of which the stop counter abutment can also be shifted. Due to the shifting, the stop counter abutment can be shifted or is shiftable into a position facing the stop abutment. The stop abutment can be formed, for example, on the first element or on an inner periphery of the first element. The engagement element can correspond, for example, to one point, and the guide track can correspond to the other point, wherein the points can repeatedly traverse their guide tracks, in particular circular guide tracks, until they come in mutual contact, which has the effect that the stop element can then be shifted. The stop counter abutment can thus be moved, for example, repeatedly, past the stop abutment, until the engagement element engages in the at least one guide track, as a result of which it is shifted along the main or secondary rotation axis, resulting in the stop abutment and the stop counter abutment facing in peripheral direction.

In particular, between the first element and the stop element, a pretensioned spring, in particular a compression spring, can be arranged, which shifts the stop element towards the offset end, when the engagement element is in the at least one guide track, whose end is offset.

Alternatively or additionally, the second engagement structure, in particular the guide track, can be a helical toothing, and the first element and the stop element can be in frictional engagement. Preferably, the first and second sliding surfaces are adapted to one another in such a manner that they generate a slightly increased friction in comparison to smooth surfaces. This can be achieved, for example, in that the first and second sliding surfaces are structured so that they engage in one another, but can nevertheless slide against each other about the secondary rotation axis. The first element can also turn the stop element due to the frictional engagement, when the engagement element is in the at least one guide track, whose end is arranged with offset, provided that the first element is turned in the first direction of rotation. As a result, the engagement element follows the helical guide track, resulting in the stop element being moved along the at least one helical guide track, in particular with a combined rotation and axial movement. This results in particular in that the stop element is moved towards the offset end. As a result, the stop counter abutment can be shifted into a position in which it faces the stop abutment in peripheral direction.

When the stop counter abutment faces the stop abutment, the general effect is that the stop counter abutment is pushed in peripheral direction against the stop abutment, if one tries to turn the first element in the first direction of rotation. Here, a turning of the first element in the first direction of rotation is blocked.

In another example, the first engagement structure can have or be a front toothing and, in addition, preferably an inner toothing. The second engagement structure can be a front toothing, wherein it is preferable that the sleeve-shaped stop element have, along the secondary rotation axis, a partial or preferably continuous slot, wherein one of the walls of the stop element bordering the slot forms the stop counter abutment. In this embodiment, it is particularly preferable that the secondary rotation axis be arranged angularly offset with respect to the main rotation axis.

In a second aspect, the sleeve-shaped stop element, by means of which the first element and the second element are coupled, has an inner toothing, wherein the stop element forms a stop counter abutment. The first element and the second element are moreover coupled via a flexible sleeve, which has an outer toothing, which engages in the inner toothing of the sleeve-shaped stop element. The first element preferably forms two sliding surfaces, which stretch the flexible sleeve in the shape of an oval. Preferably, the two sliding surfaces of the first element abut against the inner periphery of the flexible sleeve. When the first element is turned relative to the second element in the first direction of rotation or in the second direction, the two sliding surfaces slide on the inner periphery of the flexible sleeve. As a result, the flexible sleeve is deformed, wherein, in particular, it remains stretched in the shape of an oval. In the areas in which the two siding surfaces abut against the flexible sleeve, the outer toothing of the flexible sleeve is pushed into the inner toothing. In the remaining areas, the outer toothing is not in engagement with the inner toothing. In particular, the number of teeth of the outer toothing is lower, for example, one, two or three teeth lower than the number of teeth of the inner toothing.

As a result, the turning of the first element relative to the second element is transmitted with reversal of direction of rotation onto the sleeve-shaped stop element. The sleeve-shaped stop element thus turns in the second direction of rotation, when the first element is turned in the first direction of rotation, wherein the stop element turns in the first direction of rotation, when the first element is turned in the second direction of rotation.

In particular, on the second element, the stop abutment is formed, wherein, during the turning of the first element in the first direction of rotation, the stop counter abutment executes a movement towards the stop position, in particular in the second direction of rotation, wherein, in the stop position, the stop counter abutment strikes the stop abutment and prevents the turning of the first element relative to the second element in the first direction of rotation. For the sake of completeness, it is mentioned that, during the turning of the first element in the second direction of rotation, the first stop counter abutment executes a movement away from the stop position.

The drive formed thereby in the dosing mechanism is designed based on a sliding-wedge drive, which is also known under the name "harmonic Drive®."

Both for the first and for the second aspect, it is preferable that the dose-setting element be rotatable. It can be axially fixed relative to the housing or longitudinally movable. For example, during the turning movement, the dose-setting element can execute a longitudinal movement, for example, a screwing movement.

The dose-setting element can be sleeve-shaped and located, for example, in the area of the proximal end of the injection device. Alternatively or additionally, the dose-setting element can be arranged within the housing of the device, wherein the housing and the dose-setting element can be sleeve-shaped. It is conceivable that the user does not have direct access to the dose-setting element, but accesses it instead via additional parts. In principle, the dose-setting element can be designed in the form of multiple parts, for example, parts that execute rotational or translational movements, wherein a one-part dose-setting element is also conceivable. The dose-setting element located within the housing can be a dose indicator sleeve, for example, which can be read from the outside through an opening or a window, for example. In general, the dose-setting element is connected or coupled to a dose indicator sleeve.

The first element and/or second element is/are preferably sleeve-shaped and/or it/they can turn about a common rotation axis, in particular a main rotation axis, wherein this rotation axis faces, for example, in the longitudinal direction of the injection device or in the direction of the needle. The first element and the second element can be arranged concentric with respect to one another.

The first element can be connected, in exemplary embodiments, to a spring, in particular to a torsion spring or a compression spring, which stores the energy needed for the dose discharge. It is preferable that the spring can be tensioned by the dose-setting movement of the dose-setting element or of the first element. In principle, the spring can be helical or preferably spiral-shaped. The spring can be wound from a wire or preferably from a band-shaped material, in particular spring steel. Such springs are also referred to as clock springs. At least one of the dose indicator sleeve, the first element and the dose-setting element can be coupled during the dose setting in a rotationally fixed manner to an end of the spring, wherein the other end of the spring can be connected advantageously to the housing. For the dose discharge, the first element and the dose indicator sleeve can be or become engaged in a rotationally fixed manner to an end of the spring, wherein the dose-setting element is disengaged, for example.

The dose indicator sleeve can have, for example, a thread, in particular an inner or outer thread, which engages in the housing or in an element fixed to the housing, in order to be able to carry out a screwing movement for the dose indication. The dose indicator sleeve can have a scale that is arranged on its outer periphery and helical in accordance with the thread pitch. The dose indicator sleeve can have abutments acting, in particular, in the axial direction or preferably in the peripheral direction, which can strike corresponding counter abutments, for example, of the housing. The dose indicator sleeve can move back and forth between these abutments, so that, using said dose indicator sleeve, doses from 0 to the desired maximum dose, for example, 60 or 80 international units can be set, in particular provided that the stop element is not in the stop position. Thus, a maximum settable dose can be limited, on the one hand, with the abutment of the dose indicator sleeve, or, on the other hand, with the stop element, depending on which of the two elements first prevents a dose increase, i.e., a turning of the dose-setting element or of the first element in the first direction of rotation.

It is generally preferable that the second element be coupled in a rotationally fixed manner to a driven element, in particular a piston rod or threaded rod, in such a manner that, in particular, for product discharge, the driven element can be screwed in the discharge direction. For this purpose, the driven element can comprise, for example, a thread, by means of which it engages with the housing or an element fixed to the housing, in order to be able to carry out the screwing movement. For example, the second element can be coupled in the shape of a sleeve, and in a torque-proof and axially shiftable manner, to the driven element. The driven element can execute a longitudinal movement relative to the second element. The second element can be engaged indirectly or directly with the driven element; in particular, it can be in direct engagement with the driven element. For example, the second element can be coupled via a sleeve, in particular via a coupling sleeve, in a rotationally fixed or longitudinally slidable manner to the driven element. The second element can be engaged in a rotationally fixed and longitudinally slidable manner to the sleeve, which can be arranged between the driven element and the second element, for example, via a longitudinal groove. This has the advantage that when the product container is replaced, the second element does not need to execute or does not execute an axial movement relative to the first element, wherein the driven element and optionally the sleeve surrounding the driven element can be axially movable relative to the second element.

BRIEF DESCRIPTION OF THE DRAWINGS

FIGS. 2A-2C are different views of an injection device, which comprises the inventive dosing mechanism of the first embodiment in a start state, FIGS. 6A-6C and 7A-7E are different views of a third embodiment, FIGS. 8 and 9A-9C are different views of a fourth embodiment, FIGS. 11A-11C are different views of the embodiment from FIG. 10 in a start position, FIGS. 12A-12C are the views from FIG. 11 in a stop position, FIGS. 13A-13B are different views of the essential parts of a sixth embodiment, FIGS. 14A-14E is the embodiment from FIGS. 13A and 13B in different views in a start position, FIGS. 15A-15D are the views from FIGS. 14A-14D in a stop position, FIGS. 16A-16B are different views of the essential parts of a seventh embodiment, FIGS. 17A-17E are different views of the embodiments from FIGS. 16A and 16B in a start position, FIGS. 18A-18D are the views from FIG. 17A-17D in a stop position, FIG. 19 is a perspective view of the essential parts of an eighth embodiment, FIGS. 20A-20C are different views of the embodiment from FIG. 19 in a start position, FIGS. 21A-21C are the views from FIGS. 20A-20C in a stop position, FIG. 22A is an exploded view of the essential part of a ninth embodiment, FIG. 22B is the view from FIG. 22A, wherein the individual parts are represented in cross section, FIGS. 23A-23D are different views of the embodiment from FIGS. 22A and 22B, FIGS. 25A-25C are different views of the embodiment from FIG. 24 in a start position, and FIGS. 25D-25F are the views from FIG. 25A-25C, respectively, in a stop position.

DETAILED DESCRIPTION

Figure 1:
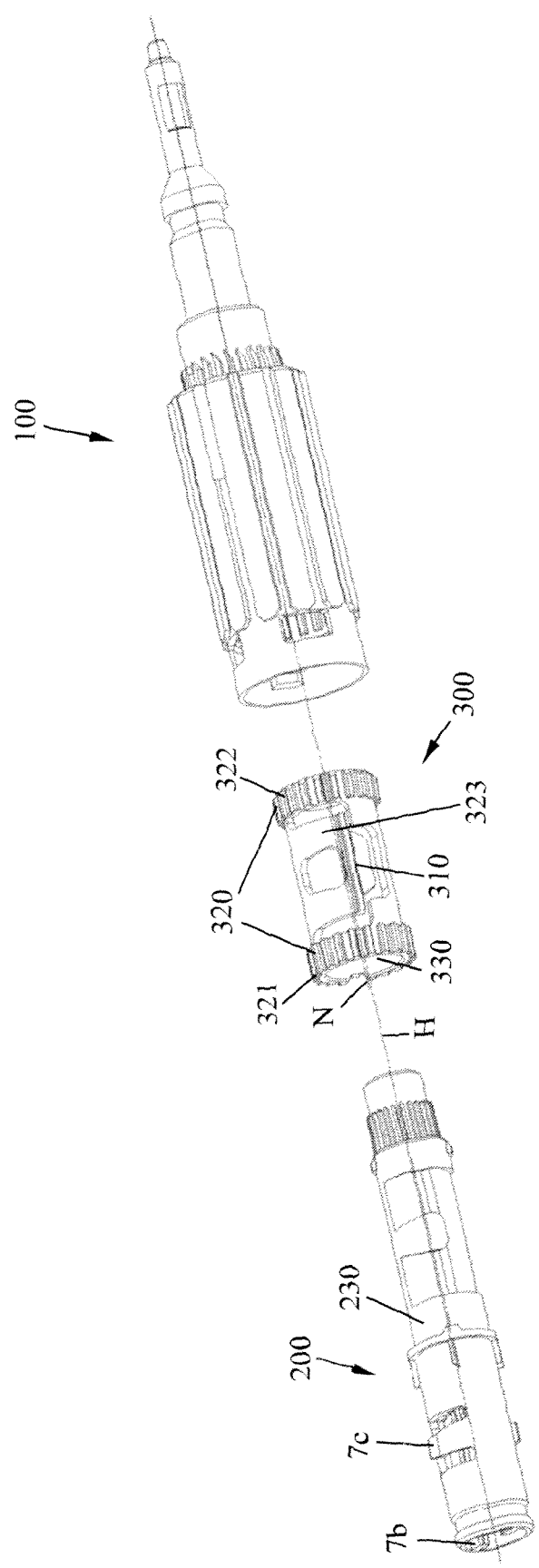
FIG. 1 is an exploded view of the essential parts of a first embodiment of the invention.

The dose mechanism according to the invention can be implemented, in general, at any site of an injection device, in which a first element 100 and a second element 200 are present, wherein, during a dose setting, the first element 100 is turned relative to the other, second element 200 about a rotation axis H in a first direction of rotation, and, during a dose discharge, it is fixed in rotation relative to the second element 200 or rotationally at rest. These first and second elements 100, 200 can be coupled via a sleeve-shaped stop element 300, which forms a stop counter abutment 310.

In this sense, the injection device shown in FIGS. 2A-2C and 3A-3C should be understood to be merely an advantageous example, since the invention can also be used in a plurality of other injection devices, as long as the first element 100 is turned relative to the second element 200 during the dose setting and is rotationally at rest during the product discharge with respect to the second element 200.

In reference to FIGS. 2A-2C and 3A-3C, the dosing mechanism is referred to as a drive and dosing device and it forms an injection device or at least is a portion of such an injection device. The drive and dosing device comprises a sleeve-shaped housing 1, which comprises an outer sleeve 1g and connected to the latter and arranged concentrically thereto an inner sleeve 1h. The inner sleeve 1h and the outer sleeve 1g are firmly connected via an annular web. The housing 1, in particular the inner sleeve 1h, has an inner thread 1a, which engages in an outer thread 3c of the threaded rod 3a, so that the threaded rod 3a and thus the driven element 3 can be screwed relative to the housing 1 about and along the (main) rotation axis H in the distal direction. The driven element 3 comprises the threaded rod 3a and a plate-shaped flange 3b, which is attached, in particular snapped in, in a manner so it can rotate freely on the distal end of the threaded rod 3a. The threaded rod 3a comprises at least one guidance groove 3d, which is superposed on the outer thread 3c and which extends parallel to the main rotation axis H. A sleeve-shaped rotation element 7, which corresponds to the second element 200 in the sense of the present invention, comprises at least one web-shaped engagement element 7b on its inner periphery, and the engagement element engages in the guidance groove 3d, as a result of which the rotation element 7 and the driven element 3 are fixed in rotation relative to one another and axially shiftable. On its outer periphery, the rotation element 7 has an annular groove 7d, into which a protuberance if formed on the inner periphery of the housing 1, in particular on the inner sleeve 1h, engages, as a result of which the rotation element 7 is rotatable relative to the housing 1 and axially fixed. A turning of the rotation element 7 produces a turning of the driven element 3, as a result of which the driven element 3 is movable along the main rotation axis H due to the thread engagement with the housing 1. For example, the driven element 3 is moved in the distal direction, when the rotation element 7 is turned relative to the housing 1 in a second direction of rotation about the main rotation axis H.

The rotation element 7 has a second coupling structure 7a in the form of an outer toothing (i.e., teeth).

On its outer periphery, the housing 1, in particular the inner sleeve 1h, has an engagement structure, wherein this engagement structure and a groove or rib-shaped longitudinal guidance 11e formed on the inner periphery of the shifting element 11 engage in one another in such a manner that the shifting element 11 is arranged in a torque-proof manner relative to the housing 1 about the main rotation axis H and shiftable along the main rotation axis H. On its inner periphery, the shifting element 11 has an inner toothing into which a latching means 7c, which is formed resiliently on the rotation element 7, engages. The latching means 7c comprises a latching arm, on the outer side of which an engagement cam is arranged, which engages in the inner toothing. When the rotation element 7 is turned relative to the shifting element 11, the latching means 7c slides over the inner toothing, as a result of which, for example, the product discharge can be signaled by means of an acoustic and/or tactile signal.

In a variant, the engagement of the latching means 7c in the inner toothing 11f can be such that the rotation element 7 can be turned only after a certain limit torque relative to the housing 1 or to the shifting element 11 has been overcome. As a result, the engagement of the latching means 7c in the inner toothing 11f prevents the driven element 3 from twisting accidentally relative to the housing 1, for example, due to vibrations during the transport of the drive and dosing device. By adjusting the latching means 7c and the inner toothing 11f, the limit torque is configured so that it can be overcome without problem by a torque generated by a rotationally pretensioned drive spring 5 during the product discharge.

However, in FIGS. 2A-2C and 3A-3C, another preferred variant is shown in which the latching means 7c (FIG. 1) and the inner toothing 11f are used merely to generate an acoustic and/or tactile signal during the product discharge. The shifting element 11 forms a seventh coupling structure by inner toothing 11f. The rotation element 7 forms an eighth coupling structure 7e in the form of a toothing, in particular an outer toothing, which is separate from the second coupling structure 7a. The seventh coupling structure, i.e., inner toothing 11f, and the eighth coupling structure 7e form the fourth coupling 7e, 11f.

The fourth coupling 7e, 11f is engaged when the activation element 8 is non-activated, and disengaged when the activation element 8 is activated, i.e., depressed. When the fourth coupling 7e, 11f is engaged, the seventh coupling structure, inner toothing 11f, and the eighth coupling structure 7e engage in one another in a torque-proof manner.

On its proximal end, the shifting element 11 has an annular groove, into which a protuberance on the inner periphery of a drive element 4, which corresponds to the first element 100 in the sense of the invention, engages, as a result of which the drive element 4 is rotatable relative to the shifting element 11 and axially fixed. A shifting of the drive element 4 along the main rotation axis H thus also produces a shifting of the shifting element 11 along the main rotation axis H. The drive element 4 has a first coupling structure 4a in the form of an inner toothing, which together with the second coupling structure 7a forms a first coupling 4a, 7a. The drive element 4 can be shifted from a disengaged position, in which the first coupling structure 4a and the second coupling structure 7a do not engage in one another, into an engaged position along the main rotation axis H, in which the first coupling structure 4a and the second coupling structure 7a engage in one another in a positive-locking connection. The drive element 4 is rotatable relative to the rotation element 7 about the main rotation axis H, when the first coupling 4a, 7a is disengaged, and it is arranged in a torque-proof manner relative to the rotation element 7 about the main rotation axis, when the first coupling 4a, 7a is engaged.

The drive element 4 has a latching structure 4d, which is formed resiliently on the drive element 4. The latching structure has at least one tooth, which is in engagement with a toothing, in particular of the second coupling structure 7a of the rotation element 7, when the first coupling 4a, 7a is disengaged. The latching structure 4d latches via the toothing, in particular the second coupling structure 7a of the rotation element 7, when the drive element 4 is twisted relative to the rotation element 7 during the setting of a product dose to be discharged in a first direction of rotation and/or a second direction of rotation. As a result, on the one hand, click sounds are generated, which signal to the user the setting of the dose in a tactile and/or acoustic manner, and which, on the other hand, predetermine discrete angular positions for the drive element 4 with respect to the rotation element 7.

The rotatable drive element 4 has a fourth coupling structure 4b, which is formed as an outer toothing. The fourth coupling structure 4b, together with a third coupling structure 2b formed as an inner toothing, forms a second coupling 2b, 4b. On the housing 1, a sleeve-shaped dose-setting element 2 is fastened, wherein the dose-setting element 2 is rotatable relative to the housing 1 and axially fixed. The dose-setting element 2 comprises an outer sleeve and an inner sleeve, which are firmly connected to one another via a web. On its inner periphery, the dose-setting element 2, in particular the outer sleeve, has a protuberance 2a, which engages in an annular groove of the housing 1, in particular of the outer sleeve 1g, so that the dose-setting element 2 is rotatable relative to the housing 1 and axially fixed.

The dose-setting element 2, in particular its inner sleeve, forms the third coupling structure 2b. The third coupling structure 2b engages in a positive-locking connection in the fourth coupling structure 4b, when the second coupling 2b, 4b is engaged, as a result of which the dose-setting element 2 is connected in a rotationally fixed manner about the main rotation axis H to the drive element 4. The drive element 4 thus also executes the rotation movements of the dose-setting element 2. When the second coupling 2b, 4b is disengaged, the third coupling structure 2b and the fourth coupling structure 4b do not engage in one another, so that the dose-setting element 2 and the drive element 4 are twistable relative to one another.

For the setting of a product dose to be discharged, the dose-setting element 2 is turned relative to the housing 1 in order to increase the dose in a first direction of rotation and, for decreasing or correcting the dose, it is turned in a second direction of rotation. During the dose setting, the second coupling 2b, 4b is engaged, as a result of which the drive element 4 also executes the rotation movements of the dose-setting element 2.

The dose-setting element 2 is arranged on the proximal end of the housing 1 and it can be gripped by the user of the device and twisted relative to the housing 1.

The proximal end of the drive and dosing device is formed by an activation element 8, which is designed as an activation button. The activation element 8 can be shifted from a non-activated position (see FIGS. 2A-2C and 3A-3C, for example) into an activated position (not shown) against a resetting spring 9, resulting in the resetting spring 9 being tensioned. The resetting spring 9 is a spiral-coiled or helical spring, which acts as compression spring, and which is arranged with its distal end against the dose-setting element 2 and with its proximal end against the activation element 8. When the activation element 8 is depressed, for example, with the thumb finger of the hand that grips the housing 1, the spring 9 is tensioned as a result. By releasing the activation element 8, the pretensioned spring 9 can push the activation element 8 from the activated position back into the non-activated position.

The activation element 8 can be shifted relative to the dose-setting element 2 along the main rotation axis H, namely between the activated position and the non-activated position. The activation element 8 is designed in the form of several parts and comprises a connecting element 8a, which has a sleeve-shaped section that is narrowed or closed at the distal end by an inward protruding collar. The proximal end of the connecting element 8a is closed by means of a covering cap 8b, which is also part of the activation element 8 and which forms a support surface for the thumb for activating the activation element 8.

The activation element 8, in particular the sleeve-shaped section of the connecting element 8a, surrounds the drive spring 5 on the peripheral side. The drive spring 5 is a spring wound in the shape of a spiral from a band-shaped material and can also be referred to as a clock spring. A first section, in particular a first end of the drive spring 5, is fastened to the activation element 8, in particular on its cylindrical section. A second section, in particular a second end of the drive spring 5, is fastened to the drive element 4, in particular between its proximal end 4c and a collar 4e. Between the first section and the second section, the drive spring 5 has a third section, which is resiliently deformed, in the case of a change of the spring tension. A turning of the drive element 4 relative to the activation element 8 produces a change in the spring tension, in particular a decrease in spring tension with the discharge of the potential energy stored by the spring 5 to the drive element 4 in the form of kinetic energy, i.e., rotation energy. The drive element 4 comprises, in particular, a rod- or pin-shaped section, which extends through the collar on the distal end of the activation element 8 into the interior of the activation element 8 and through the drive spring 5. The proximal end 4c narrows towards the proximal end of the drive and dosing device, for example, in the shape of a sphere, cone or truncated cone. The activation element 8, in particular the covering cap 8b, forms a contact surface 8d for the proximal end 4c of the drive element 4.

Figure 3A:
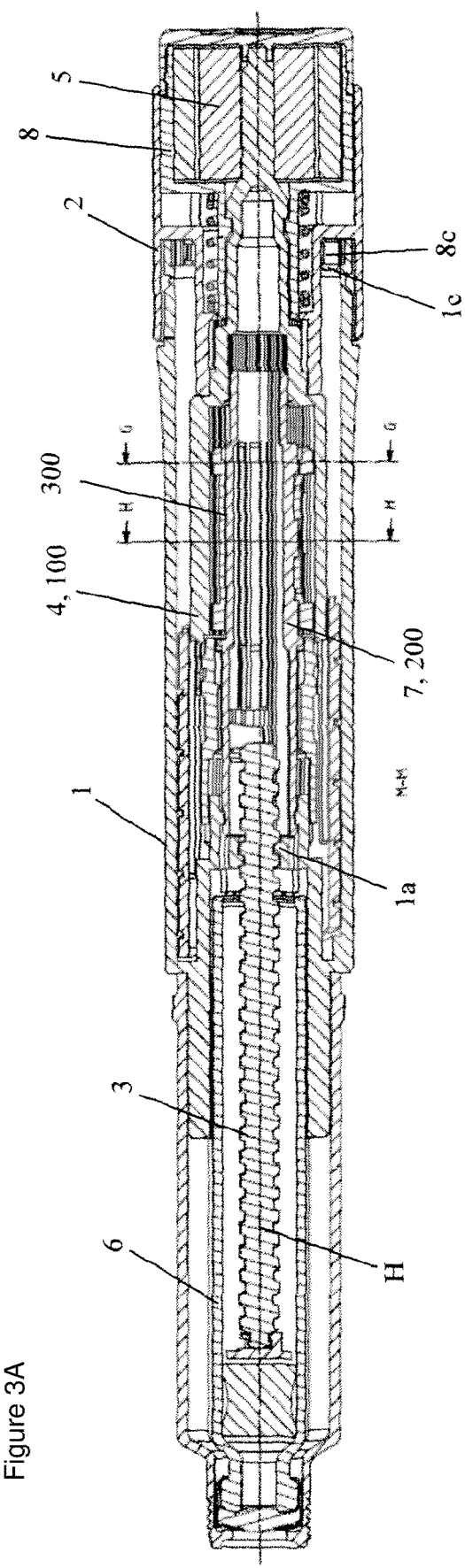
FIGS. 3A-3C are the views of FIGS. 2A-2C, wherein a stop counter abutment strikes a stop abutment and blocks the further dose increase.
Figure 3C:
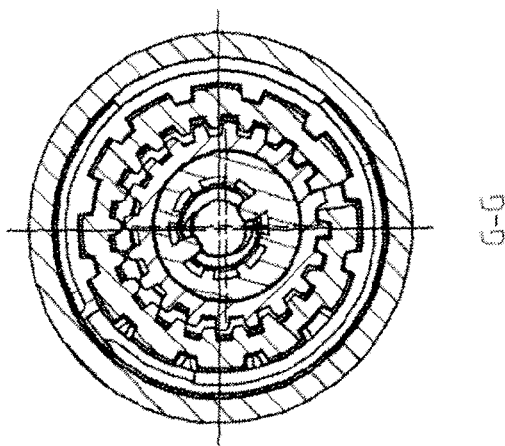
Figure 3B:
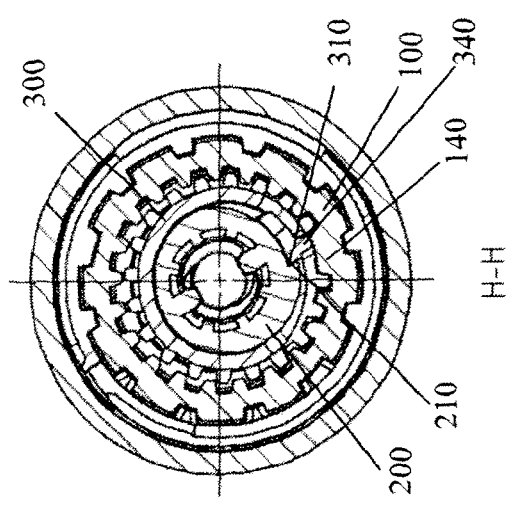
Figure 4:
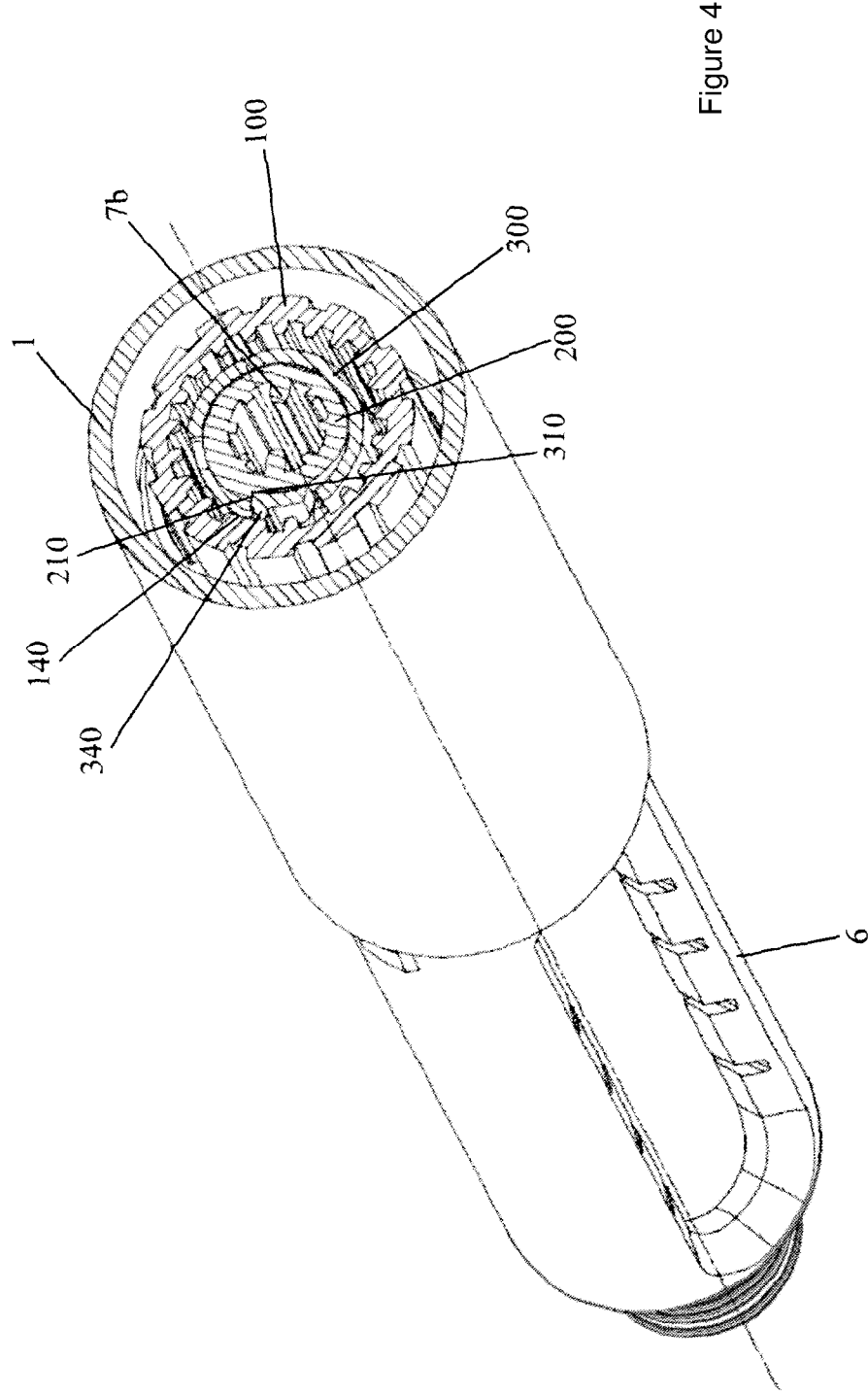
FIG. 4 is a cross-sectional perspective view of the section H-H from FIG. 3A, FIGS. 5A-5C are different views of a second embodiment.

The activation element 8, in particular the connecting element 8a, comprises a sixth coupling structure 8c in the form of an outer toothing, which is formed, for example, on a protuberance protruding in the distal direction. The protuberance engages through the collar that connects the inner sleeve to the outer sleeve of the dose-setting element 2. The housing 1, in particular the outer sleeve 1g, has a fifth coupling structure 1c, which is formed as an inner toothing and which, together with the sixth coupling structure 8c, forms a third coupling 1c, 8c (FIG. 3A). By activating the activation element 8, the third coupling 1c, 8c can be engaged, and by releasing the activation element 8a, it can be disengaged. When the third coupling 1c, 8c is engaged, the sixth coupling structure 8c engages in a form-fitting connection in the fifth coupling structure 1c, as a result of which the activation element 8 and, in particular, also the dose-setting element 2, which is connected in a rotationally fixed manner to the activation element 8, is fixed in rotation with respect to the housing 1. The activation element 8 and the dose-setting element 2 are rotatable relative to the housing 1, when the third coupling 1c, 8c is disengaged, wherein the sixth coupling structure 8c and the fifth coupling structure 1c then do not engage in one another.

On the distal end of the housing 1, a sleeve-shaped product container holder 12 is fastened, in particular nondetachably, in which a product container 6 is accommodated. In the example shown, the product container 6 is a cartridge. The product container 6 comprises a container body 6a, which holds a liquid product to be administered, wherein, in the container body 6a, proximally with respect to the product, a shiftable piston 6b is arranged, which is in sealing contact with the inner wall of the container body 6. On the distal end of the container body 6a, a septum 6c is formed, which can be perforated by means of a needle that can be arranged on a thread 12c of the product container holder 12. With the shifting of the piston 6b in the direction of the septum 6c, the product contained in the product container 6 is discharged via the needle.

The product container holder 12 has a window through which the product quantity contained in the product container 6 can be visually monitored. The product container holder 12 has a recess into which a first engagement structure is snapped on the inner periphery of the housing 1, in particular of the outer sleeve 1g, when the product container holder 12 is fastened to the housing 1. The product container holder 12 comprises, on its outer periphery, a peripherally extending collar, which is applied on the distal end of the housing 1, in particular of the outer sleeve 1g, when the product container holder 12 is fastened to the housing 1. On its outer periphery, the product container holder 12 has a cam to which a sleeve-shaped cap, which can be shifted over the product container holder 12, can be snapped detachably. The cap can thus be removed again and it is used merely for protecting an optionally arranged needle and/or the medicament from exposure to light. For the snap connection to the cam, the cap has a recess, in particular a groove, arranged in the shape of a ring on the inner periphery.

The drive and dosing device comprises a sleeve-shaped stop element 300, which may also be referred to as dose limiter 13, which couples the first element 100 or drive element 4 to the second element 200 or rotation element 7. On the second element 200, a stop abutment 210 is formed, which is separated from a stop counter abutment 310 of the stop element 300 proportionally to the maximum quantity that can be discharged from the product container 6 or proportionally to a defined product quantity that can be discharged from the product container 6. Since, during the dose setting, the drive element 4 is twisted relative to the rotation element 7 and since it is not twisted during the dose discharge, a counter mechanism can be formed by the stop element 300, which adds the already discharged individual doses and the currently set dose, and accordingly comes increasingly closer to the stop abutment 210. The effect of a dose increase is that the stop counter abutment 310 is moved towards the stop abutment 210. A dose reduction has the effect that the stop counter abutment 310 is moved away from the stop abutment 210. If the residual dose indicated in the product container 6 is smaller than the maximum dose that can be set by means of the drive and dosing device, the stop counter abutment 310 comes in contact with the stop abutment 210, so that a twisting of the dose-setting element 2 or of the drive element 4 relative to the rotation element 7 in a direction of rotation that would result in a dose increase, i.e., in a first direction of rotation, is blocked.

A dose indicator element 10 comprises an outer thread 10b, which engages in an inner thread 11a of the housing 1. The dose indicator element 10, which is sleeve-shaped and can thus be referred to as a dose indicator drum, has a dose scale, which extends helically over its outer periphery in accordance with the pitch of the outer thread 10b and which comprises multiple scale values arranged successively. For example, by means of the drive and dosing device, a maximum dose of 80 IU can be set, wherein the scale is indicated from 0 to 80, and the dose values are indicated in steps of two.

The dose indicator element 10 has an abutment surface facing and acting in peripheral direction, which is referred to as zero-dose abutment. The dose indicator element has an additional abutment surface facing and acting in peripheral direction, and referred to as maximum dose abutment.

The dose indicator element 10 has an outer thread 10b, which is in engagement with an inner thread 11a of the outer sleeve 1g of the housing 1 or, in general, of the housing 1. The housing 1, in particular the outer sleeve 1g, has a zero dose counter abutment and a maximum dose counter abutment.

The dose indicator element 10 can be screwed back and forth between a zero dose position and a maximum dose position. In the zero dose position, the zero dose abutment, in collaboration with the zero dose counter abutment, prevents the turning of the dose indicator element 10 in a second direction of rotation, namely in a direction of rotation that would result in a dose smaller than zero being set. In this zero dose position, the dose indicator element 10 is rotatable in the opposite direction, i.e., the first direction of rotation.

In the maximum dose position, the maximum dose abutment, in collaboration with the maximum dose counter abutment, prevents the turning of the dose indicator element 10 in the first direction of rotation, which would result in an increase of the dose above the maximum settable value. The turning in the second direction of rotation is possible in the maximum dose position.

The housing 1, in particular the outer sleeve 1g, has an indicator device in the form of a window that makes it possible to view the dose scale of the dose indicator element 10. The dose indicator element 10 is connected to the driver member 4 in a rotationally fixed and axially shiftable manner. For this purpose, the dose indicator element 10 comprises at least one, in this example several guidance grooves 10c extending parallel to the main rotation axis H. Protuberances 4f on the outer periphery of the drive element 4 engage in these guidance grooves 10c.

FIGS. 2A-2C and 3A-3C show a delivery state of the device, in which the activation member 8 is non-activated. In the indicator device, the dose zero appears, i.e., showing that the dose indicator element 10 is in its zero dose position.

The drive spring 5 is prestressed with sufficient energy so that the product quantity contained in the product container 6 can be completely discharged with the energy stored in the spring 5 by shifting the piston 6b, in particular in one or in several individual discharges, between which, in each case, a new dose setting occurs, without tensioning the spring 5. In the delivery state, the first coupling 4a, 7a is disengaged, the second coupling 2b, 4b is engaged, and the third coupling 1c, 8c is disengaged. The drive spring 5 is switched kinematically between the drive element 4 and the dose setting element 2. The second coupling 2b, 4b prevents the turning of the drive element 4 relative to the dose setting element 2.

For setting or increasing the product dose to be discharged, the dose setting element 2 is turned relative to the housing 1 in a first direction of rotation, as a result of which the drive element 4, the spring 5, and the dose indicator element 10 are also turned. Due to the turning, the dose indicator element 10 is screwed away from the zero dose counter abutment, wherein the distance measured between the zero dose abutment and the zero dose counter abutment along the screwing curve is proportional to the product dose to be discharged. Due to the indicator element 10, the currently set dose can be read off in IU. If the dose has been set inadvertently excessively high, then the dose setting element 2 can be turned by turning in the opposite direction of rotation, i.e., in the second direction of rotation relative to the housing 1, as a result of which the distance between the zero dose abutment and the maximum dose abutment decreases, and the set dose is reduced.

For the product discharge, the activation element 8 is pushed, for example, with the thumb of the hand that grips the housing 1 from a non-activated position into an activated position, as a result of which the resetting spring 9 is tensioned. During the movement of the activation member 8 from the non-activated position into the activated position, first the third coupling 1c, 8c is engaged, so that the drive spring 5 is switched kinematically between the housing 1 and the drive element 4. The dose setting element 2 is then also arranged in a torque-proof manner with respect to the housing 1. If the activation member 8 is pushed farther in the distal direction to the activated position, the first coupling 4a, 7a is engaged, as a result of which the rotation element 7 is arranged in a torque-proof manner with respect to the drive element 4. Further shifting of the activation member 8 to an activated position results in the second coupling 2b, 4b being disengaged, so that the torque of the drive spring 5 is led via the fourth coupling 7a, 11f into the housing 1, as a result of which the drive spring 5 cannot yet be untensioned. It is only when the fourth coupling 7a, 11f is disengaged, once the activated position of the activation member 8 has been reached, that the drive spring 5, which is arranged with its first end against the housing 1, is able to release the spring energy stored in it in the form of rotation energy via the drive element 4 to the rotation element 7, as a result of which the drive element 4 turns in the second direction of rotation. In the process, the rotation element 7 also turns in the second direction of rotation, with the result that the drive element 3 is also turned in the second direction of rotation and thereby is screwed on the inner thread 1a in the distal direction, as a result of which the piston 6e is moved in the distal direction, and the product contained in the product container 6 is discharged. Due to the rotationally fixed connection between the drive element 4 and the dose setting element 10, the dose indicator element 10 is screwed back into its zero dose position at the same time. When the zero dose abutment strikes the zero dose counter abutment, the set dose has been discharged completely, wherein, due to the striking of the zero dose abutment against the zero dose counter abutment, the dose indicator element 10 is stopped in terms of its turning, as a result of which the drive element 4 is also stopped in terms of its turning in the second direction of rotation. When the user releases the activation member 8, the resetting spring 9 resets the activation member 8 into its non-activated position, wherein the first coupling 4a, 7a, the second coupling 2b, 4b, the third coupling 1c, 8c, and the fourth coupling 7a, 11f are reset into their starting positions. By turning the dose setting element 2 in the first direction of rotation, a dose to be released can now be set again, and in turn discharged by activating the activation member 8, etc. If the product container 6 should contain a product quantity that is less than the maximum dose that can be discharged with the device, in this example, less than 80 IU, the stop counter abutment 310 strikes the stop abutment 210, when the dose setting element 2 is turned in the first direction of rotation, before the maximum dose abutment strikes the maximum dose counter abutment. As a result, the user of the device is prevented from injecting less product than he has set with the device.

In the first embodiment represented in FIGS. 1 to 4, the second element 200 has a second sliding surface 230, which, in particular, extends concentrically about a secondary rotation axis N. The second sliding surface 230 is an outer peripheral surface of the sleeve-shaped second element 200. The sleeve-shaped stop element 300 has a first sliding surface 330, which is an inner peripheral surface. The first sliding surface 330 can slide rotatingly on the second sliding surface 230. In other words, the sleeve-shaped stop element 300 with its first sliding surface 330 is mounted rotatably about the secondary rotation axis N on the second sliding surface 230. The secondary rotation axis N is arranged eccentric, i.e., parallel and at a distance with respect to the main rotation axis H. During the product discharge, the second element 200 can be rotated about the main rotation axis H, wherein the secondary rotation axis N arranged eccentrically thereto also rotates about the main rotation axis H.

The sleeve-shaped stop element 300 surrounding the second element 200 has, over its outer periphery, a first engagement structure 320, which is formed as an outer toothing. The first engagement structure 320 has a first section 321 and a second section 322, which are offset from one another along the secondary rotation axis N, i.e., they are spaced apart. The area between the first and second sections 321, 322 can work without the first engagement structure 320. The sleeve-shaped stop element 300 has a stop counter abutment 310 that forms a stop counter abutment surface that preferably faces in peripheral direction. The stop counter abutment 310 is arranged resiliently transversely with respect to the peripheral direction, between the first section 321 and the second section 322. The stop counter abutment 310 is formed on a resilient tongue 323, which extends, for example, in peripheral direction, forming an integral part with the stop element 300. The stop counter abutment 310 can thus also be moved towards the secondary rotation axis N and away from the secondary rotation axis N.

In particular, the first engagement structure 320 extends concentrically about the secondary rotation axis N. On its inner periphery, the first, sleeve-shaped element 100 has a second engagement structure 120, which is formed as inner toothing and which extends concentrically about the main rotation axis H. During the dose setting, the first element 100 can be turned about the main rotation axis H relative to the second element 200. During the dose discharge, the first element 100 together with the second element 200 can be turned about the main rotation axis H. The first sleeve-shaped element 100 surrounds the stop element 300 and at least the second sliding surface 230 of the second element. Between the first element 100 and the second element 200, an annular gap is thus formed, in which the stop element 300 is arranged, as one can see best in FIGS. 2B-2C and 3B-3C. As a result of the stop element 300 being sleeve-shaped, it is advantageously achieved that the stop element 300 can surround the driven element 3 or the threaded rod 3a, often also referred to as piston rod. As a result, a space-saving arrangement is achieved.

Due to the eccentric arrangement of the stop element 300 with respect to the main rotation axis H, it is advantageously achieved that the engagement structure 320 is in a positive-connection operational engagement, i.e., intermeshes, in only a small area of the periphery with the second engagement structure 120. In terms of construction, this is the site where the pitch circle of the first engagement structure 320 and of the second engagement structure 120 are in contact. The pitch circle diameter of the first engagement structure 320 is smaller than the pitch circle diameter of the second engagement structure 120. Over most of the periphery, the engagement structures 120, 320 are not in operational engagement. As a result of the fact that the engagement structures 120, 320 engage in one another in a positive-lock connection in the engagement area, the stop element 300 turns with the same peripheral speed as the first element 100, as a result of which the stop element 300 turns during the dose setting with another, in particular greater, angular speed than the first element 100.

The second element 200 has a stop abutment 210 that forms a stop abutment surface that preferably faces in the peripheral direction. The stop abutment surface leads to the second sliding surface 230. A recess is located in the sliding surface 230 in front of the stop abutment surface in peripheral direction. On its inner periphery, the first element 100 has a switch structure 140 in the form of a protuberance. The stop element 300, in particular the stop counter abutment 310, has a switch counter structure 340 in the form of an outward protruding protuberance. The switch structure 140 and the switch counter structure 340 move each on a circular path during the dose setting. Each of the switch structure and the switch counter structure can traverse repeatedly through its self-enclosed path. Due to the different angular speeds, the switch structure 140 and the switch counter structure 340 reach an abutting position, as a result of which the switch structure 140 deflects the switch counter structure 340 and thus also the stop counter abutment 310 transversely with respect to the peripheral direction and, in particular, with respect to the secondary rotation axis N, in particular into the recess that is located in front of the stop abutment surface. As a result, the stop abutment 210 and the stop counter abutment 310 face one another in peripheral direction, so that the stop counter abutment 310 can be pushed against the stop abutment 210, as a result of which a turning of the stop element 300 in the first direction of rotation is prevented (FIGS. 3A-3C and 4).

The second embodiment, which is shown in FIGS. 5A-5C, is similar, in principle, to the first embodiment, wherein the stop element 300 differs substantially in its shape. For example, the first element 100 can correspond to the dose setting element 2 shown in FIGS. 2A-2C, wherein the second element 200 can be the housing 1, for example. Other positions for the stop element 300 in an injection device are naturally also conceivable. The stop element 300 is a slit sleeve. It has a slot 324, which extends continuously over the entire length of the stop element 300, i.e., from the distal end to the proximal end. The slot can be arranged at an inclination or parallel with respect to the main or secondary rotation axis H, N. The slot 324 is bordered on both sides in each case by a wall of the stop element 300. One of the walls forms the stop counter abutment 310. The second element 200 has a section that has a second sliding surface 230, which is formed as outer peripheral surface and arranged concentric about the secondary rotation axis N. The stop element 300 has a first sliding surface 330, which is formed as inner peripheral surface and arranged concentric about the secondary rotation axis N. The stop element 300 is rotatably mounted with its first sliding surface 330 about the secondary rotation axis N on the second sliding surface 230, i.e., eccentrically with respect to the main rotation axis H.

The stop element 300 has a first engagement structure 320, which extends over the outer periphery of the stop element 300 concentrically about the secondary rotation axis N and which is formed, in particular, as a toothing.

On its inner periphery, the first sleeve-shaped element 100 comprises a second engagement structure 120, which extends concentrically about the main rotation axis H and which is formed, in particular, as a toothing. The first element 100 can be mounted, for example, concentrically, in particular rotatably and in an axially fixed manner on a section of the second element, which is arranged concentric with respect to the main rotation axis H. The second element 200 comprises a stop abutment 210 with a stop abutment surface facing in peripheral direction, a recess being located in the second sliding surface 230 in front of said stop abutment surface.

On its inner periphery, the first element 100 has a switch structure 140, formed as a protuberance, for example. The switch structure 140 can be formed, for example, by filling the gap between two teeth of the toothing.

On its outer periphery, the stop element 300 has a switch counter structure 340, which forms a protuberance, for example. The switch counter structure 340 is arranged in the area of the first engagement structure 320, wherein the switch structure 140 is arranged in the area of the second engagement structure 120. During the dose setting, in particular during the turning of the first element 100 relative to the second element 200 in the first direction of rotation, the switch structure 340 and the switch counter structure 140 can traverse their respective circular path, in particular repeatedly, until they finally strike one another as can be seen, for example, in the representation in which the stop position in FIG. 5C is shown, as a result of which the switch counter structure 340 is deflected transversely with respect to the peripheral direction towards the secondary rotation axis N. As a result, the stop counter abutment 310 with its stop counter abutment surface is also deflected transversely with respect to the peripheral direction towards the secondary rotation axis N. The switch structure 140 pushes the switch counter structure transversely with respect to the peripheral direction into the recess that is located in front of the stop abutment 210. The stop abutment 210 and the stop counter abutment 310 thus face one another, resulting in the stop counter abutment 310 being pushed against the stop abutment 210, as a result of which a turning of the first element 100 relative to the second element 200 in the first direction of rotation is prevented.

In the third embodiment shown in FIGS. 6A, 6B and 7A-7E, the first element 100 can correspond, for example, to the dose-setting element 2 from FIGS. 2A-2C, and the second element 200 can correspond, for example, to the housing 1, wherein the embodiment is not limited to this.

The second element 200 is sleeve-shaped and, over its outer periphery, it has a second engagement structure 220 in the form of an outer toothing. The second engagement structure 220 is arranged concentric about the main rotation axis H. The first element 100 is rotatable relative to the second element 200 about the main rotation axis H, and, in particular, it is mounted in an axially fixed and rotatable manner on the second element 200. On its inner periphery, the first element 100 has a second sliding surface 130, which is arranged concentric with respect to the secondary rotation axis N. Preferably, the outer peripheral surface of the first element 100 is arranged concentric with respect to the main rotation axis H.

The first element 100 comprises a stop abutment 110 with a stop abutment surface, which faces, in particular, in peripheral direction. In the second sliding surface 130, a recess is located in front of the stop abutment 110 or the stop abutment surface in the peripheral direction.

On its inner surface, the sleeve-shaped stop element 300 has a first engagement structure 320, which is formed as an inner toothing. The first engagement structure 320 extends concentrically about the secondary rotation axis N. The stop element 300 is mounted with its first sliding surface 330, which is formed as an outer peripheral surface, rotatable about the secondary rotation axis N on the second sliding surface 130.

On its inner periphery, the stop element 300 has a switch counter structure 340, which is preferably formed as a protuberance. The second element 200 has a switch structure 240, which is formed on its outer periphery, wherein the switch structure 240 is preferably formed as a protuberance and, in the particular case, consists of two teeth that are at a smaller distance apart in comparison to the tooth gaps of the remaining toothing.

The stop element 300 has a first section that extends continuously over the periphery and, separately therefrom, a second section that forms the stop counter abutment 320 and the switch counter structure 340. The sections are arranged mutually offset along the secondary rotation axis N. The stop element 300 has a slot 324 that extends only in part over the entire length of the stop element 300. The slot 324 makes it possible for the stop counter abutment 320 to be resiliently deflectable relative transversely with respect to the peripheral direction. The stop counter abutment 320 is formed on a resilient arm, which makes it possible to deflect the stop counter abutment 320 transversely with respect to the peripheral direction. On the arm, the stop counter abutment 320 and the switch counter structure 340 are formed. One of the walls, which borders the slot 324, forms the stop counter abutment 320.

During the dose setting, the first element 100 is turned relative to the second element 200 in the first direction of rotation about the main rotation axis H. In the process, the sliding surface 130 arranged concentric with respect to the main rotation axis H also rotates about the main rotation axis, as a result of which the secondary rotation axis N also rotates about the main rotation axis H. In the process, the stop element 300 shifts in the second direction of rotation on the second element 200. When, during the further course, the switch counter structure 340 abuts against the switch structure 140 or comes in contact (see stop positions in FIGS. 7B-7E), the switch counter structure 340 including the stop counter abutment 310 is deflected away from the switch structure 140 transversely with respect to the peripheral direction outward, i.e., away from the secondary rotation axis N. As a result, the stop counter abutment 310 and the stop abutment 110 face one another in the peripheral direction, and, as a result, the stop counter abutment 310 is able to strike the stop abutment 110 and prevents the turning of the first element 100 relative to the second element 200 in the first direction of rotation.

The fourth embodiment from FIGS. 8 and 9A-9C functions similarly to the third embodiment, and therefore only the differences are explained. The stop element 300 has a continuous slot. The switch counter structure 340 is in the form of a first protuberance that is offset from the first engagement structure 320 along the secondary rotation axis N. The second element 200 has a switch structure 240 that is offset from the second engagement structure 220 and in the form of a protuberance extending from the front side of the second element 200 in the direction of secondary rotation axis N. The embodiment from FIGS. 9A-9C thus has a stop plane and a counter plane, wherein, in the counter plane, the first engagement structure 320 and the second engagement structure 220 are arranged, and wherein, in the stop plane, the switch structure 240 and the switch counter structure 340 are arranged. The stop abutment surface of the stop abutment 110 and the stop counter abutment surface of the stop counter abutment 310 can be located in the stop plane and/or in the counter plane.

The fifth embodiment represented in FIGS. 10, 11A-11C, and 12A-12C comprises a sleeve-shaped second element 200, which has a second engagement structure 220 in the form of several teeth distributed regularly or irregularly over the periphery (FIGS. 11A-11C and 12A-12C). The distance between adjacent teeth of the second engagement structure 220 is greater than the distance between adjacent teeth of the first engagement structure 320 of the stop element 300, which is also formed in the shape of a sleeve.

The second engagement structure 220 extends concentrically about the main rotation axis H and is arranged in the inner periphery of the second element 200.

The first sleeve-shaped element 100 is connected via an annular peripheral collar, which engages in an annular groove of the second element 200, in an axially fixed manner and rotatably about the main rotation axis H to the second element 200. The second sliding surface 130 of the first element 100 is formed as an outer peripheral surface and extends concentrically about the secondary rotation axis N. The secondary rotation axis N is arranged parallel and at a distance with respect to the main rotation axis H.

On its inner periphery, the sleeve-shaped stop element 300 has a first sliding surface 330, which extends concentrically about the secondary rotation axis N and by means of which the stop sleeve is mounted rotatably on the second sliding surface 130 about the secondary rotation axis N. The stop counter abutment 310 is arranged with offset along the secondary rotation axis N with respect to the first engagement structure 320. The stop counter abutment 310 is formed on a resilient tongue 323, which extends in the peripheral direction. The second element 200 forms the stop abutment 210. The stop abutment 210 is formed by an end of a groove extending over a portion of the periphery of the second element. In contrast to the first to fourth embodiments, the resilient tongue 323 is deflected only during the installation, wherein the stop counter abutment 310 in the form of a protuberance engages in the groove of the second element 200, which extends partially over the periphery, and remains there. The second engagement structure 320 is arranged concentric about the secondary rotation axis N.

The dosing mechanism has a stop plane and a counter plane, which can be seen in FIGS. 11B-11C and 12B-12C. The stop plane and the counter plane each are arranged normal with respect to the main or secondary rotation axis H, N. The groove extending partially over the periphery, the stop abutment 210, and the stop counter abutment 310 are arranged in the stop plane. In the counter plane, which is at a distance from the stop plane, the first engagement structure 320 and the second engagement structure 220 are arranged.

The stop element 300 is arranged in the annular gap formed between the first element 100 and the second element 200. During the turning of the first element 100 relative to the second element 200 about the main rotation axis H, the secondary rotation axis N and the second sliding surface 130 arranged concentrically thereto turn about the main rotation axis H in the first direction of rotation, as a result of which the stop element 300 turns about the secondary rotation axis N in the opposite direction of rotation, i.e., in the second direction of rotation. As a result, the stop counter abutment 310 is turned closer to the stop abutment 210, as can be seen in comparison to the start position with the stop position (FIGS. 11C and 12C in the stop plane). When the stop counter abutment 310 strikes the stop abutment 210, the turning of the first element 100 relative to the second element 200 in the first direction of rotation is also blocked.

Figure 10:
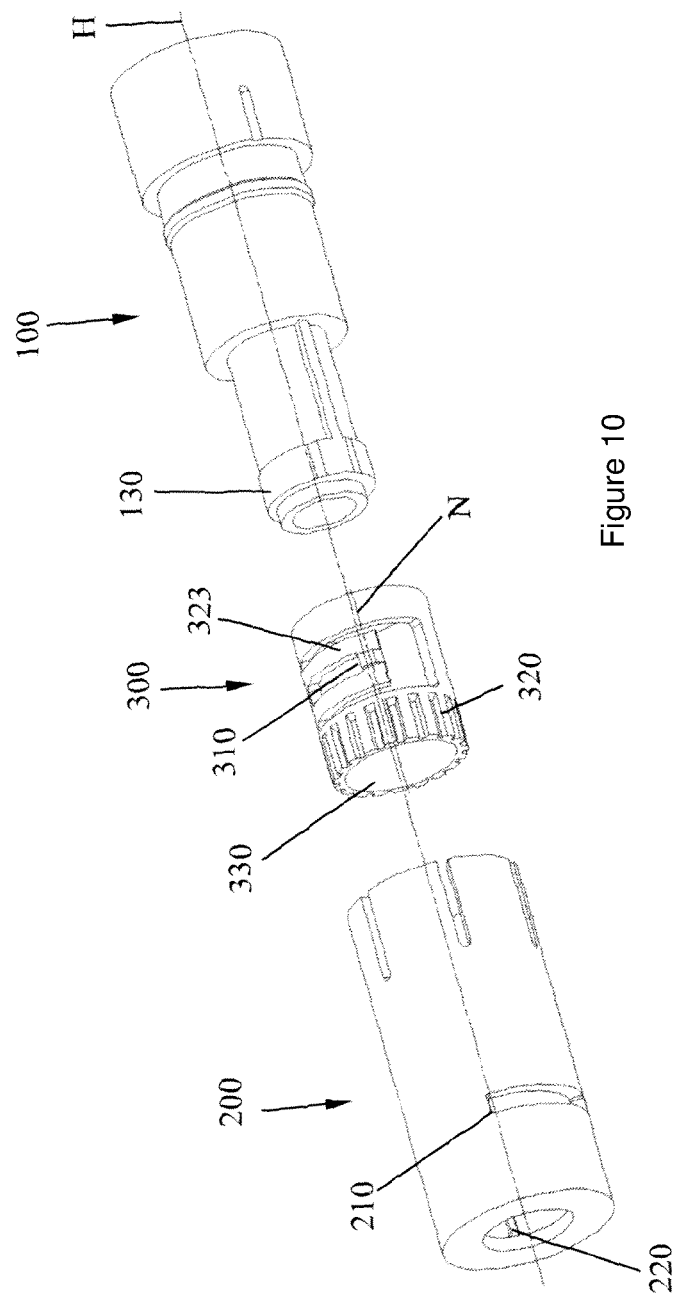
FIG. 10 is an exploded view of the essential parts of a fifth embodiment.
Figure 24:
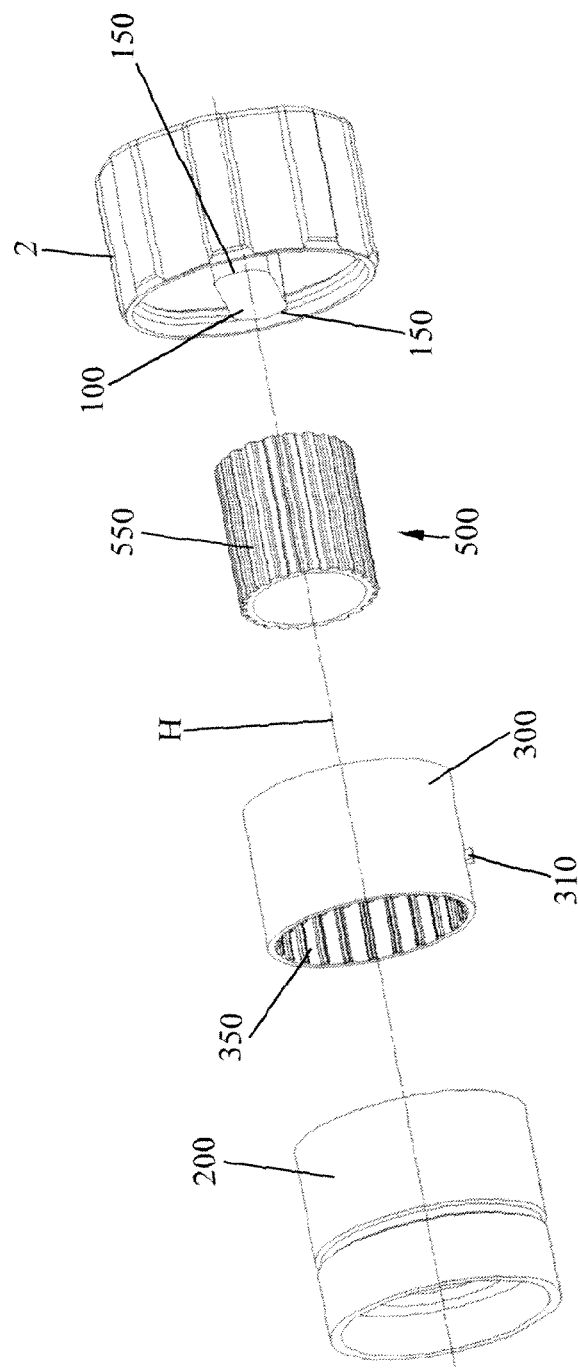
FIG. 24 is a perspective view of the essential parts of a tenth embodiment.

As can be seen best in FIG. 10, the sliding surface 130 is an annular peripheral collar, wherein a web, which extends approximately parallel to the main or secondary rotation axis H, N, extends from the annular peripheral collar. This web is used to stabilize the stop element 300 so that it does not tilt transversely with respect to the secondary rotation axis N. The solution using the web allows a simple installation and a saving of material and it has advantages in the production by injection molding.

The sixth embodiment from FIGS. 13a to 15 has a sleeve-shaped second element 200 and a sleeve-shaped first element 100, which is connected, in particular snapped-in, by means of an annular collar engaging in an annular groove, in an axially fixed and rotatable manner to the second element 200. The first element 100 is rotatable relative to the second element 200 about the main rotation axis H. The second element 200 has a second engagement structure 220 that is arranged over its outer periphery, and that is formed as an outer toothing and comprises a plurality of guide tracks. The stop element 300 has a first engagement structure 320 arranged over its inner periphery. The second engagement structure 220 is arranged concentric with respect to the main rotation axis H, wherein the first engagement structure 320 is arranged concentric about the secondary rotation axis N, which is arranged eccentric with respect to the main rotation axis H. Over its outer periphery, the sleeve-shaped stop element 300 has a first sliding surface 330 arranged concentric with respect to the secondary rotation axis N. On its inner periphery, the first sleeve-shaped element 100 has a second sliding surface 130 arranged concentric with respect to the secondary rotation axis N, on which sliding surface the stop element 300 is mounted slidingly over its first sliding surface 330 so it can rotate about the secondary rotation axis N. A pretensioned spring 400, which preferably acts as compression spring, is operably arranged (e.g., braced) between the first element 100 and the stop element 300. The spring 400 tries to shift the sleeve-shaped element 300 from the start position shown in FIGS. 14B and 14E along the secondary rotation axis N into a stop position in which the stop counter abutment 310 faces the stop abutment 110 of the first element 100 in peripheral direction. The movement of the stop element 300 along the secondary rotation axis N is then released, when an engagement element 326, which is formed on the inner periphery of the stop element 300, engages in a certain guide track of the engagement structure 220. If this is not the case, the stop element 300 cannot be shifted.

The end 223 of at least one of the guide tracks 221 is arranged along the main rotation axis H or secondary rotation axis N with an offset towards the ends 222 of the other guide tracks 221. The at least one guide track 221, which has the offset end 223, can be referred to as the long guide track, to improve the discriminability. The other guide tracks 221 with the ends 220 can be referred to as short guide tracks. The stop element 300 preferably has multiple engagement elements 326 distributed over its periphery, in particular a sufficient number so that one of the engagement elements 326 is always in engagement with the guide tracks 221. As a result, it is ensured that the stop element 300 can be axially shifted only when the engagement element 326 is in the long guide track. In the start position, the engagement element 326 is in a short guide track. The first element 100 can be turned about the main rotation axis H relative to the second element 200 in the first direction of rotation, wherein the engagement element 326 moves on a path associated with it. After a certain turning, in particular several rotations of the first element 100 about the main rotation axis H, the engagement element 326 comes to be in engagement with the long guide track. As long as the engagement element 326 is in a short guide track, the end 220 prevents the stop element 300 from being shifted axially. Since the end 223 of the long guide track is offset with respect to the ends 222 of the short guide tracks, the stop element 300 can be shifted axially. The stop counter abutment 310 is then shifted thereby into a stop plane, in which the stop abutment 110 is also located. In other words, the stop counter abutment 310 faces the stop abutment 110 in peripheral direction, so that a rotation of the first element 100 relative to the second element 200 about the first direction of rotation pushes the stop counter abutment 310 against the stop abutment 110, as a result of which a rotation of the first element 100 relative to the second element 200 in the first direction of rotation is prevented or blocked.

If the set dose is to be corrected, for example, by turning the first element 100 back relative to the second element 200 in the second direction of rotation, the first element 100 and the stop element 300 can be adjusted to one another in such a manner that a turning pushes the stop element 300 back along the secondary rotation axis N and in the process tensions the spring 400 again.

The seventh embodiment, which is represented in FIGS. 16A, 16B, 17A-17E, and 18A-18D, corresponds basically to the sixth embodiment, wherein the seventh embodiment works without the spring 400 but instead comprises a second engagement structure 220 in the form of a helical toothing, which is arranged concentric about the main rotation axis H, toothing that comprises guide tracks 221 arranged helically about the main rotation axis H. Furthermore, the first sliding surface 330 and the second sliding surface 130, which are arranged concentric about the secondary rotation axis N, are adjusted to one another in such a manner that the friction between the first element 100 and the stop element 300 is increased slightly, which makes it possible for the first element 100 and the stop element 300 to turn as well, due to the frictional engagement, when the engagement element 326 is in the guide track 221, whose end 223 is arranged with offset (long guide track), and the first element 100 is turned in the first direction of rotation or, for dose correction, in the second direction of rotation.

The first engagement structure 320 of the stop element 300 is arranged concentric with respect to the secondary rotation axis N over the inner periphery of the stop element 300. On the inner periphery there is at least one engagement element 326, which in principle has the same function as the engagement element 326 from the sixth embodiment.

In the start position, as represented in FIGS. 17C-17D, the at least one engagement element 326 is in a short guide track, i.e., in a guide track with the ends 222.

The first element 100 can be turned relative to the second element 200 about the main rotation axis H in the first direction of rotation, wherein at least one of the engagement elements 326 is in a short guide track, wherein the end 222 prevents the stop element 320 from being shifted along the secondary rotation axis N. As long as the engagement element 326 is in one of the short guide tracks, the second sliding surface 130 can slide on the first sliding surface 330. The stop abutment 110 and the stop counter abutment 310 are located in different positions along the secondary rotation axis N, so that the stop counter abutment 310 can be moved past the stop abutment 110 at least once, preferably repeatedly. In the further course of the turning of the first element 100 in the first direction of rotation, the engagement element 326 engages in the long guide track, whose end 223 is arranged axially offset with respect to the ends 222 of the short guide tracks. By means of the frictional engagement of the second sliding surface 130 with the first sliding surface 330, the stop element 300 is shifted helically along the main rotation axis H or secondary rotation axis N, i.e., screwed. As a result, the stop counter abutment 310 is shifted into a position in which it faces the stop abutment 110 in peripheral direction. A further turning of the first element 100 in the first direction of rotation results in the stop counter abutment 310 being pushed against the stop abutment 110, as a result of which a turning of the first element 100 relative to the second element 200 in the first direction of rotation is prevented.

For dose correction, the first element 100 can be turned relative to the second element 200 in the opposite, i.e., second direction of rotation, as a result of which, due to the frictional engagement between the first element 100 and the stop element 300, the stop element 300 is screwed back along the main or secondary rotation axis H, N.

The eighth embodiment shown in FIGS. 19, 20A-20C, and 21A-21C comprises a first sleeve-shaped element 100, a second sleeve-shaped element 200, and a sleeve-shaped stop element 300. The first element 100 is rotatable about the main rotation axis H relative to the second element 200, and, in particular, it is connected in an axially fixed and rotatable manner to the second element 200. The stop element 300 has a first sliding surface 330, which is arranged concentric about the secondary rotation axis N, which is arranged at an acute angle with respect to the main rotation axis H, and which preferably intersects the main rotation axis H or alternatively is arranged at an inclination thereto. The first sliding surface 330 is an inner peripheral surface. The second sliding surface 230, which is formed by the second sleeve-shaped element 200, is arranged concentric about the secondary rotation axis N, and an outer peripheral surface. The stop element 300 is mounted slidingly with its first sliding surface 330 rotatable about the secondary rotation axis N on the second sliding surface 230. The first element 100 has a second engagement structure 120 in the form of a front toothing, which faces the stop element 300. The second engagement structure 120 extends concentrically about the main rotation axis H.

The stop element 300 has a first engagement structure 320 and an inner toothing. The engagement structure 320, in particular the front toothing, intermeshes with the engagement structure 120.

The first element 100 has a switch structure 140, which is formed on an outer periphery located in front of the engagement structure 120, and which protrudes radially outward. The stop element 300 has a switch counter structure 340 arranged on the inner periphery of the stop element 300.

The stop element 300 is a slit sleeve, i.e., the stop element 300 has a slot 324, which, in the example shown, extends over the entire length of the stop element 300. One of the walls of the stop element 300, which borders the slot 324, forms a stop counter abutment 310. On the end with the stop counter abutment 310, the switch counter structure 340 is also arranged.

The engagement structures 120, 320 are adjusted to one another in such a manner that the stop element 300 turns with a different angular speed, in particular a greater angular speed, about the secondary rotation axis N from the angular speed with which the first element 100 turns about the main rotation axis H. For this purpose, the first engagement structure 320 can have a lower tooth number from that of the second engagement structure 120.

During the turning of the first element 100 relative to the second element 200 about the main rotation axis H, the switch structure 140 moves on a circular path about the main rotation axis H, through which it can traverse repeatedly, for example. Furthermore, the switch counter structure 340 moves on its circular path about the secondary rotation axis N, through which it can traverse repeatedly, for example. Due to the different angular speeds, the switch structure 140 and the switch counter structure 340 come into mutual contact after a certain total rotation angle, as a result of which the switch structure 140 deflects the switch counter structure 340 and thus the stop counter abutment 310 transversely with respect to the peripheral direction and away from the secondary rotation axis N, resulting in the stop counter abutment 310 being deflected into a position in which it faces in the peripheral direction the stop abutment 210, which is formed by the second element 200. By turning the first element 100 relative to the second element 200 in the first direction of rotation, the stop counter abutment 310 is pushed against the stop abutment 210, as a result of which a further turning of the first element 100 relative to the second element 200 about the main rotation axis H is prevented or blocked (FIGS. 21A-21C).

The ninth embodiment shown in FIGS. 22A, 22B, and 23A-23D comprises a sleeve-shaped first element 100 and a sleeve-shaped second element 200, wherein the sleeve-shaped first element 100 surrounds the sleeve-shaped second element 200 surrounds. The sleeve-shaped second element 200 can be, for example, in a direct torque-proof and axially shiftable engagement with a piston rod. In an annular gap between the sleeve-shaped first element 100 and the sleeve-shaped second element 200, a sleeve-shaped stop element 300 is arranged, which is rotatable about a secondary rotation axis N. The first sleeve-shaped element 100 can correspond, for example, to the drive member 4, and the second sleeve-shaped element 200 can correspond, for example, to the driven element 3 of the injection device from FIGS. 2A-2C and 3A-3C.

In FIGS. 22A and 22B, the stop element 300 is represented turned around. The engagement structure 320 would have to face in the proximal direction, in order to be able to engage with the engagement structure 120 in an engagement. The second element 200 has a sliding surface 230 that is arranged concentric about the secondary rotation axis N and formed as an outer peripheral surface. The stop element 300 has a first sliding surface 330 arranged concentric with respect to the secondary rotation axis and formed as an inner peripheral surface. The stop element 300 has a first engagement structure 320 in the form of an outer toothing that can be arranged concentric with respect to the secondary rotation axis N. On its inner periphery, the first element 100 has a second engagement structure 120 that is formed as a toothing and arranged concentric with respect to the main rotation axis H. This stop element 300 surrounds the second element 200. To that extent, this embodiment can be compared to the first embodiment.

On its inner periphery, the first element 100 has a switch structure 140, wherein the stop element 300, on its outer periphery, has a switch counter structure 340. Each of the switch structure 140 and the switch counter structure 340 can traverse its respective path, preferably repeatedly, until the switch structure 140 and the switch counter structure 340 strike one another. When the switch structure 140 and the switch counter structure 340 strike one another, the stop element 300 is tilted about a tilt axis that is arranged transversely with respect to the secondary rotation axis N and main rotation axis H. As a result, the secondary rotation axis N is also tilted with respect to the main rotation axis H. Since the stop counter abutment 310 is arranged preferably rigidly on the stop element 300, the stop counter abutment 310 is tilted with the stop element 300.

On its second sliding surface 230, the second element 200 has a recess that is located in front of the stop abutment 210 in the peripheral direction. When the stop element 300 is moved, in particular tilted, into its deflected position, the stop counter abutment 310 moves in peripheral direction in front of the stop abutment 210, as a result of which the stop counter abutment 310 strikes the stop abutment 210 and prevents the rotation of the first element 100 relative to the second element 200 in the first direction of rotation.

In the undeflected position of the stop element 300 or when the switch structure 140 and the switch counter structure 340 do strike one another, the secondary rotation axis N can be parallel to the main rotation axis H or it can be freely tiltable with respect to the main rotation axis H. If, in the process, and when the first element 100 turns relative to the second element 200 in the first direction of rotation, the stop counter abutment 310 and the stop abutment 210 come in contact, their shaping results in the resetting of the stop element 300 into the undeflected position. The secondary rotation axis N is then tilted or kept tilted inevitably with respect to the main rotation axis H, when the switch structure 140 and the switch counter structure 340 strike one another. In particular, between the first element 100 and the second element 200, the annular gap is dimensioned in terms of its gap width in such a manner that the stop element 300 can tilt about the tilt axis.

The embodiments 1 to 9 are configured based on the first aspect described herein.

The tenth embodiment shown in FIGS. 24 and 25A-25F, which is configured based on the second aspect described herein, comprises a first element 100, a second sleeve-shaped element 200, a sleeve-shaped stop element 300, and a flexible sleeve 500. The flexible sleeve 500 is connected in a rotatably fixed manner to the second element 200. The first element 100 is rotatable about the main rotation axis H relative to the second element. A secondary rotation axis is not required. The first element 100 is coupled via the sleeve-shaped stop element 300 and the flexible sleeve 500. The first element 100 can be coupled, in particular connected or formed as a single part, with a dose setting element 2, which is sleeve-shaped.

The sleeve-shaped stop element 300 has an inner toothing 350 (i.e., teeth), which, in particular, extends concentrically about the main rotation axis H. The stop element 300 forms a stop counter abutment 310, preferably on its outer periphery. The flexible sleeve 500 comprises an outer toothing 550, which engages in the inner toothing 350 or intermeshes with the inner toothing 350. The first element 100 forms two sliding surfaces 150, which are stretched over the flexible sleeve 500 in the shape of an oval, in particular stretched approximately in the shape of an ellipse, and which slide on the inner periphery of the flexible sleeve 500, when the first element 100 is turned relative to the second element 200 in the first direction of rotation. As a result of the flexible sleeve 500 being flexible, it is deformed when the first element 100 is turned relative to the second element 200. The number of teeth of the outer toothing 550 is preferably smaller than the number of teeth of the inner toothing 350.

The second element 200 forms a second sliding surface 230, which is formed as inner peripheral surface. The stop element 300 forms a first sliding surface 330, which is formed as outer peripheral surface. The stop element 300 is slidingly mounted on the second sliding surface 230 in a manner so it can rotate about the main rotation axis H. Due to the lower number of teeth of the flexible sleeve 500, the stop counter abutment 310 is moved in the second direction of rotation or towards the stop abutment 210 formed by the second element 200, when the first element 100 is turned in the first direction of rotation.

When the stop counter abutment 310 reaches its stop position, i.e., when it strikes or comes in contact with the position in which the stop counter abutment 310 strikes or comes in contact with the stop abutment 210, the turning of the stop sleeve 300 in the second direction of rotation is blocked, as a result of which the turning of the first element 100 in the first direction of rotation is also blocked, since a turning of the first element 100 in the first direction of rotation requires that the stop element 300 be rotatable in the second direction of rotation opposite the first direction of rotation.

It is mentioned merely as an example that the first element 100 can correspond to the dose setting member 2 (FIGS. 2A-2C and 3A-3C). The second element 200 can correspond, for example, to the housing 1.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A dosing mechanism for an injection device, comprising:
   a dose-setting element coupled to a first element, which, during a dose setting, is rotatable relative to a second element about a main rotation axis in a first direction of rotation and, during a dose discharge, is fixed in rotation relative to the second element, wherein the first element and the second element are coupled via a sleeve-shaped stop element, which forms a stop counter abutment and which surrounds at least one of the first element or the second element; and
   a stop abutment, wherein the stop counter abutment, during a rotation of the first element in the first direction of rotation moves to a stop position in which the stop counter abutment strikes the stop abutment and prevents the rotation of the first element relative to the second element in the first direction of rotation, and
   wherein the sleeve-shaped stop element is rotatable about a secondary rotation axis that is offset parallel to or offset at an angle to the main rotation axis, and
   wherein the first element is connectable to a spring which stores the energy needed for the dose discharge.

2. A dosing mechanism according to claim 1 wherein the spring can be tensioned by a dose-setting movement of the dose-setting element or of the first element.

3. A dosing mechanism according to claim 2 wherein the spring is selected from a torsion spring, a compression spring, a helical spring, a spiral spring or a clock spring.

4. A dosing mechanism according to claim 3 wherein at least one of a dose indicator sleeve, the first element and the dose-setting element can be coupled during the dose setting in a rotationally fixed manner to an end of the spring.

5. A dosing mechanism according to claim 4 wherein the other end of the spring can be connected to a housing.

6. A dosing mechanism according to claim 4, wherein for the dose discharge, the first element and the dose indicator sleeve can be or become engaged in a rotationally fixed manner to an end of the spring, wherein the dose-setting element is disengaged.

7. The dosing mechanism of claim 1, wherein a first engagement structure is arranged over a periphery of the stop element and is concentric about the secondary rotation axis,
   wherein a second engagement structure is arranged over a periphery of one of the first element and the second element about the main rotation axis, and
   wherein the first engagement structure and the second engagement structure engage in a positive-locking connection in an engagement area.

8. The dosing mechanism of claim 7, wherein the first engagement structure comprises a toothing, and wherein the toothing intermesh with the second engagement structure in the engagement area.

9. The dosing mechanism of claim 7, wherein the second engagement structure is arranged over an inner periphery of the first element,
   wherein the first engagement structure is arranged over an outer periphery of the stop element,
   wherein the first engagement structure comprises a first section and a second section that are offset with respect to one another along the secondary rotation axis, and
   wherein the stop counter abutment is arranged between the first section and the second section.

10. The dosing mechanism of claim 7, wherein the second engagement structure is arranged over an inner periphery of the first element,
    wherein the first engagement structure is arranged over an outer periphery of the stop element,
    wherein, along the secondary rotation axis, the sleeve-shaped stop element comprises a partial or continuous slot,
    wherein a wall of the stop element borders the slot and forms the stop counter abutment, and
    wherein the second element forms the stop abutment and/or the stop element surrounds the second element.

11. The dosing mechanism of claim 7, wherein the second engagement structure is arranged over an outer periphery of the second element,
    wherein the first engagement structure is arranged over an inner periphery of the stop element,
    wherein, along the secondary rotation axis, the sleeve-shaped stop element comprises a partial or continuous slot,
    wherein a wall of the stop element borders the slot and forms the stop counter abutment, and
    wherein the first element forms the stop abutment and/or the stop element surrounds the second element.

12. The dosing mechanism of claim 11, wherein the stop abutment is formed by the first element,
    wherein the stop element comprises a switch counter structure arranged on an inner periphery and is offset from the first engagement structure,
    wherein the second element comprises a switch structure offset from the second engagement structure, and
    wherein the switch structure resiliently deflects the switch counter structure and the stop counter abutment during rotation of the first element transversely with respect to the peripheral direction such that the stop counter abutment faces the stop abutment.

13. The dosing mechanism of claim 7, wherein the second engagement structure is arranged over an inner periphery of the second element,
    wherein the first engagement structure is arranged over an outer periphery of the stop element, and
    wherein, along the secondary direction of rotation, the stop counter abutment is arranged offset with respect to the first engagement structure,
    wherein the stop counter abutment is arranged on a resilient tongue, and
    wherein the second element forms the stop abutment and/or the stop element surrounds the first element.

14. The dosing mechanism of claim 7, wherein the second engagement structure is arranged over an outer periphery of the second element,
    wherein the first engagement structure is arranged over an inner periphery of the stop element,
    wherein the second engagement structure comprises a plurality of guide tracks arranged over a periphery, each having a front-side end,
    wherein an end of at least one of the guide tracks is arranged along the main rotation axis or along the secondary rotation axis offset with respect to the ends of the other guide tracks,
    wherein the first engagement structure comprises at least one engaging element, and
    wherein the stop element is movable along the main rotation axis or along the secondary rotation axis relative to the second element when the engaging element is in the guide track such that the stop counter abutment can be shifted in a position facing the stop abutment.

15. The dosing mechanism of claim 14, wherein the guide tracks of the second engagement structure comprise a helical toothing, wherein the first element and the stop element are in a frictional engagement, and wherein the first element turns the stop element due to the frictional engagement when the engaging element is in the guide track and the first element is turned in the first direction of rotation such that the stop element is moved towards the offset end.

16. The dosing mechanism of claim 15, wherein a pretensioned spring is arranged between the first element and the stop element, and wherein the spring shifts the stop element towards the offset end when the engaging element is in the guide track.

17. The dosing mechanism of claim 16, wherein the stop counter abutment is arranged on the sleeve-shaped stop element such that it can be resiliently deflected, and wherein one of the first and second elements comprises a switch structure, which resiliently deflects the stop counter abutment during the turning of the first element transversely with respect to the peripheral direction such that the stop counter abutment faces the stop abutment.

18. The dosing mechanism of claim 7, wherein the first engagement structure is a front toothing and/or an inner toothing, and the second engagement structure is a front toothing, wherein along the secondary rotation axis, the sleeve-shaped stop element comprises a partial or continuous slot, and wherein one of the walls of the stop element enclosing the slot forms the stop counter abutment.

19. The dosing mechanism of claim 7, wherein the stop counter abutment of the sleeve-shaped stop element can be tilted about a tilt axis that is transverse relative to the main rotation axis and the secondary rotation axis, wherein one of the first element and the second element comprises a switch structure, and during rotation of the first element, the switch structure tilts about the tilt axis such that the stop counter abutment faces the stop abutment.

20. The dosing mechanism of claim 1, wherein the stop element comprises a first sliding surface, wherein one of the first element and the second element comprises a second sliding surface, and wherein at least one of the first and second sliding surfaces is arranged concentric about the secondary rotation axis, and the first sliding surface and the second sliding surface slide off one another rotatingly during the turning of the first element.

21. The dosing mechanism of claim 1, wherein the stop abutment is formed on at least one of the first or the second element.

* * * * *